US007022485B1

(12) United States Patent
Serre et al.

(10) Patent No.: US 7,022,485 B1

(45) Date of Patent: Apr. 4, 2006

(54) FIBRIN CITRULLINE DERIVATIVES AND THEIR USE FOR DIAGNOSING OR TREATING RHEUMATOID ARTHRITIS

(75) Inventors: Guy Serre, Toulouse (FR); Mireille Sebbag, Toulouse (FR)

(73) Assignee: Universite Paul Sabatier, Toulouse (FR)

(*) Notice: Subject to any disclaimer, the term of this patent is extended or adjusted under 35 U.S.C. 154(b) by 0 days.

(21) Appl. No.: 10/019,439

(22) PCT Filed: Jun. 30, 2000

(86) PCT No.: PCT/FR00/01857

§ 371 (c)(1), (2), (4) Date: May 8, 2002

(87) PCT Pub. No.: WO01/02437

PCT Pub. Date: Jan. 11, 2001

(30) Foreign Application Priority Data

Jul. 1, 1999 (FR) .................................. 99 08470

(51) Int. Cl.
*C12Q 1/68* (2006.01)
*A61K 38/04* (2006.01)

(52) U.S. Cl. ....................... 435/7.1; 530/324; 530/325; 530/326; 530/327; 530/328; 530/329; 530/330; 530/380

(58) Field of Classification Search ................ 530/327, 530/328, 380; 435/7.1, 324, 325, 326, 329, 435/330; 614/2

See application file for complete search history.

(56) References Cited

U.S. PATENT DOCUMENTS 4,281,061 A * 7/1981 Zuk et al.
5,821,068 A * 10/1998 Soe et al.
5,858,723 A * 1/1999 Mueller-Lantzsch et al.

FOREIGN PATENT DOCUMENTS

WO 95 28946 11/1995
WO 98 22503 5/1998

OTHER PUBLICATIONS

Masson-Bessiere et al. Synovial target antigens of antifilaggrin auto antibodies are deiminated forms of fibrin alpha and beta chains. Revue Du Rhumatisme, 66:754, Dec. 1999.*

Tarcsa et al. Protein unfolding by peptidylarginine deiminase. Substrate specificity and structural relationships of the natural substrates trichohyalin and filaggrin. J Biol Chem.. 271(48):30709-307016, 1996.*

Schellekens et al. Citrulline is an essential constituent of antigenic determinants recognized by rheumatoid arthritis-specific autoantibodies. J Clin Invest. 101(1):273-281, 1998. *

* cited by examiner

*Primary Examiner*—Christina Chan
*Assistant Examiner*—Maher M. Haddad
(74) *Attorney, Agent, or Firm*—Oblon, Spivak, McClelland, Maier & Neustadt, P.C.

(57) ABSTRACT

The invention concerns citrulline polypeptide derived from fibrin useful for diagnosing or treating rheumatoid arthritis.

16 Claims, 3 Drawing Sheets

Figure 1:
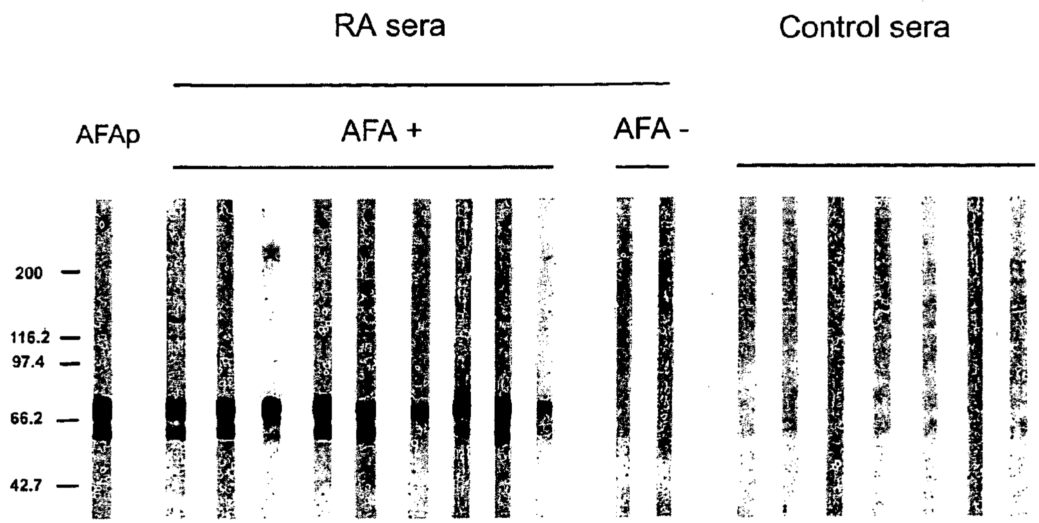

SEQUENCE LISTING

<160> NUMBER OF SEQ ID NOS: 12

<210> SEQ ID NO 1
<211> LENGTH: 5676
<212> TYPE: DNA
<213> ORGANISM: Homo sapiens

<400> SEQUENCE: 1

```
cagctgttca gggatgtctg gaaaagaagc ccacccacat tgcttctgga cactgggtgt     60
gactttggag ggtatcaggt ttgtctgtta aagaaactgc caacctcttc ctgccccaat    120
tggcctctgt tcccttgcat gccctctttc cttgggacac tcccttaagg catcttcttg    180
acattaactt aactataaat gtttatttga tgaatttcag tgacctgaag agagatggag    240
gtcaaatcag aagaagcaca tggctaaggt tgcaatgcac ttgctttttc attgaattaa    300
agtcattcga ataccattca gtttacttaa gttctaggcc cagctttact cctaatcgat    360
gtcagactgt agcaaatatt aggtccaaag ttggaagagt tagcaggatc ctctccatga    420
cagaactttg gcttccactt tactaaaata gagattgtgt ggttgagctg cagctatgta    480
cagaaaagtg tcatacaatt aaaaatcacc aaactcagtc tcttcaattt gagcaatagt    540
tggtgaattt actccaccac ctcctctcct tgaaggttct ttcctgctct cctcactata    600
aatgcaggat gacctggaaa ggctaggacc tgaggttcag ttaccctgac acaaaggaat    660
tcagtttctc tgatctcata gtcacaggct gccagagctc tacggaacat gcaagatcat    720
ctgctttaag cctcttgtgg tggcatctgt tgttttccac tgccctgtac ctattgctct    780
ttccttggtt aacagaacct ttattttctt ctgaaaactc tctgctcagt catggtaggg    840
ccatcagtcc acatgatcag gcctctcctg gccaaacatg gcatctttct tttgggaatt    900
tgaatcttaa gctgaatagc tgaagttcaa aaaaagctgt tgaatctgac ttacgcctac    960
agtggctttg caaagtgact gtccattcct atttcttaag tccctgaatt tataatttat   1020
cctggttaca gccctttctg agatgtgtgg ttttttttcc aactgtctct tatagtctgt   1080
gaattttcat atttcttttc atacattttc atgttttgtt tgtttgtttg tgtgtttttt   1140
ggctttaggt aggcagaatc agtttctgtt gtttataccc aaggaatcct gattgataca   1200
tccttcccct ttaaaaataa agtatctaag gctcaaagag agtaggctac ctgcctgagg   1260
tctgggagta agttagtacc agagctcgta ctaaccccag gttagccaac tgctttacac   1320
aacatttgct ctctccttca gagttatagc agtcttggaa gaaagaagct actattttgc   1380
caaagacctc aggaggacca agaacaagtt ctgggatatg tgatgattga actcttaaaa   1440
agtttgttgg acttctggcc ataattgtgt atctaagacc agatttcatt cttaatagct   1500
aaacaaacaa acaagagatc cacaggttca gcagctataa taagagtgaa ttactgatac   1560
agttgacaac atgaatatat ctcagaaacc atggcatcaa tgagcaaaaa aaatccagac   1620
acagaagaat acgtaccata tgcctgcatt tatgtgatat tctagcattg tattgtccaa   1680
catagtagcc agtagcctca catggctatt caaatttaag ttgattaaaa ttaagtaaga   1740
ataaaaattt agctcttcag tagcgttagc cacatgtaac tagtggctac cacatcagac   1800
ggtgcaaata tagaatattt cctttataac agaaagttct attggaaaac aatgttctag   1860
aaaatataca cataatctat aaaaacaaaa agcaagtcag tgattgtcta aggccagggg   1920
tgaggggaga tcgattgcaa agtggtatga ggaaagtttt ggggtaatag ggttgttgga   1980
atcttgattg cgatgaaggc tactcggtgt ctaatgtgtc acctcctcag actgaacact   2040
```

-continued

```
tggaattggc gaatttcatt gtatgtaaat tatacctcat aaagtaactc taagaggtca   2100
agtgttttgt ggaaattatt tttaatcagt tgcaatactt attatgagat gatttttgca   2160
aatacataaa catgttattc atccattagg tgcaatattt ttgctagctc ctgaaaacac   2220
agagatgaat tagaatagca agcctgccct caagctgttc acaatccagt acaggagatg   2280
agtctattca aaaatagcta gactccagga agaaagttat aggtgacctt acacaaaaaa   2340
gtgcagatat aattatgtag gacagtagaa gtggggaagg tttcttttat gtggaaaaaa   2400
gagggagaat ttttggtctt tgaaggatga gcaagatgtg aatatgcgca gatggagttt   2460
taaaacattc ctggtggagg gcagaatatg atccaaggca caagagcaac cagaaaaata   2520
tgcaacctag aggaaagtgc atgaagggga gcagttgtaa aataattttc atgaatgtaa   2580
gtgagaagaa tttgtatcat agacacctga gtttggcaga gtgcatgttc ttggctccta   2640
ggagtcaaga agaacaaagt gtccctttct cctacgttat gctcagtggt ccaagtccaa   2700
aacacctttc cttccttaag tactttcttc tcccctccat acaaatctaa agtcttcaca   2760
aacatcattt aaacaggcag gtcatggtca gaaaggcaat tgcttttcct agacttctat   2820
gtacgttatt atattacaat ttctgcctaa aagactctaa agtcttggaa aagtttccac   2880
cttgcacatc aaagatataa ttcatgcatt tgtatagtaa ccttagtccc ctaagagaat   2940
aaggatgaac tataaatata agaagtaatt atggtaatta taatatgatt gccacttatt   3000
tttcacttga tcgtgtatgg ttgcatgcta ctggtgttct gttgaattct agagagtttg   3060
cctctttttc ctgggtcaac tctcgccatt tatttccata atgcaatagg agccaatctt   3120
tttcataatt acttatttaa aatttgttgc catttaattt ctgttcctct tagcttagta   3180
actttaggat ttttaaataa caactattga aatcatgaca tacgtttaaa tgatattatt   3240
taaatacgtt aggctataaa ccttttaaat tttttaaaaa aatagatgag tgtggtggct   3300
catgcctgta atcccaacac tttgggaagc cgggtcggga ggatagcttg agtccagcag   3360
tttgagacca gtcagggcaa cacagcaaga ccccatatct aaaaaaaacaa aacaaaacaa   3420
aattacctgg gtatggttgt gctcacctgt agtccaagct acacaggaag ctgaggcaga   3480
aggatcactt gagcccagga ggttgaggct gcagtgatcc atgaacgcgc tgctacactc   3540
agtctgggtg acagtgcaag aagctgtctc aaaaataata aataaataaa aataactttt   3600
aaaaaacaaa aattaattaa attttaaaaa cacaacacac tagagatgtt tgcaaattga   3660
ttatttggga gtctatatcc ctggaagtta atttaaaata tttagaagag ttcttcctca   3720
tttcctagag acgtcgaatt gtaaatatca gagctagaag gaacactagg gctcgccact   3780
ccaaagtgtg gtccaaggac cagcagcatc aagtaacctg ggaacgtgtt agaaatgcag   3840
agtcttaggc ctcaccccag acctactgaa ccagaatctg cattaacaag atttctaggt   3900
gcctcacggg cacattaaaa cttgagaagc tctgcactag aaatcttcac tccacctttc   3960
attataaatg gaatcacttg ggctgtggtc acaggaaatt gattattttt aatttcagaa   4020
ccttctattt aggtcatcta tatttgctaa tagcagggaa gaaagccaaa ctctttaact   4080
gcaattaaca aatctataat taattagtta agcaatcttc cctttaagtt ttacattttg   4140
tggagcaagc tgtttgattt ggctggggct caggccggcc tgtttgtgaa tttcacaatt   4200
cacagatgtt agccgctctc gggctaagta aaggaagaga atgtcaagtt ttaaatagct   4260
tctcccttcc atcctggctg aagcaacaaa taaaatattt ttatgaaaca cattttgagt   4320
tagatttact tacagggaaa tgtcaaattt ctctgaaagg gctttagatt gtctcacaac   4380
```

```
tttgacatct actgatgtca cctatttaca ggtgtgtcct gtgactaggg ggtgaaggga   4440

agatgtgaac tcaccatgtt agtgaccgtt agatacacag agtggttttt tttcccctg    4500

ttggagtcta tcctaactga gcttctgaat catatttcat tcaatttcca aatccacaaa   4560

accaggataa gtttacagcc catattcaga aaggaaataa attattttgt gtgtagactt   4620

tcctgatatt acactgattt gggaatatat gaacaatttt atggtttcct ttcgaagtag   4680

gtcaagtcaa agcaaaacca aaaacagcaa aaactgtaag acataaagaa tagagtggag   4740

ccgactgaga gattaaaata aactagaata tttttattaa caggcaattt gaaataattt   4800

gtgcacttca gaatattcta caataatata ttatttccaa ttttaatatc tttaagaaaa   4860

ttactatatt atatgtaagt acatgtgcat gtgtttgagg taggatattt aactcaataa   4920

aggttatttt cttttattcg ggtcaggcaa agcttctaag gggatgtgaa agggatatct   4980

ctttctctta gctgagagga agagtgagtt ctaagttaaa tataatcaag gaatttccct   5040

gtctttgcta tttgagattg tgaccacaac aggcggttgg ctgaaaggga aactgaaggg   5100

cggggaggga gggaaataga tgaaaaaaca aaacaaaaca aaacttccct aagcagctct   5160

acaaaacatt ttagccccag aaatagtcac agaaatcctc aaatcaaacc agtatccaga   5220

tacaaggaag tgttatgtag ctggagcagg gtggacactc atcagctcag ttcagttaca   5280

aaagtccagg ctgctgaaat taaactctga tgccattcat gccagcatcc aatcacgaca   5340

gagatcagaa gttcagagat gcctccagct ccaaattgcc aacaacaagt gtggctacta   5400

tacgtcaagg actctgaagc cgtgagagag ggggaagaac aacagtagag aggatgccca   5460

gctggtaaga atcgagtgtt tatgaagttt tagtcaattg atgaatctca ttggctaaaa   5520

tcaagaaacg ctccgcctct ttgcaaatat gtatgaagga gagaagtgcc taaacttcta   5580

tgtctgatag catttgaccc tattgctttt agcctcccgg ctttatatct atatatacac   5640

aggtatttgt gtatatttta tataattgtt ctccgt                             5676
```

<210> SEQ ID NO 2
<211> LENGTH: 5960
<212> TYPE: DNA
<213> ORGANISM: Homo sapiens
<220> FEATURE:
<221> NAME/KEY: promoter
<222> LOCATION: (1).(5676)
<221> NAME/KEY: 5'UTR and intron
<222> LOCATION: (5677).(5960)

<400> SEQUENCE: 2

```
cagctgttca gggatgtctg gaaaagaagc ccacccacat tgcttctgga cactgggtgt     60

gactttggag ggtatcaggt ttgtctgtta aagaaactgc caacctcttc ctgccccaat    120

tggcctctgt tcccttgcat gccctctttc cttgggacac tcccttaagg catcttcttg    180

acattaactt aactataaat gtttatttga tgaatttcag tgacctgaag agagatggag    240

gtcaaatcag aagaagcaca tggctaaggt tgcaatgcac ttgctttttc attgaattaa    300

agtcattcga ataccattca gtttacttaa gttctaggcc cagctttact cctaatcgat    360

gtcagactgt agcaaatatt aggtccaaag ttggaagagt tagcaggatc ctctccatga    420

cagaactttg gcttccactt tactaaaata gagattgtgt ggttgagctg cagctatgta    480

cagaaaagtg tcatacaatt aaaaatcacc aaactcagtc tcttcaattt gagcaatagt    540

tggtgaattt actccaccac ctcctctcct tgaaggttct ttcctgctct cctcactata    600

aatgcaggat gacctggaaa ggctaggacc tgaggttcag ttaccctgac acaaaggaat    660
```

-continued tcagtttctc tgatctcata gtcacaggct gccagagctc tacggaacat gcaagatcat 720
ctgctttaag cctcttgtgg tggcatctgt tgttttccac tgccctgtac ctattgctct 780
ttccttggtt aacagaacct ttattttctt ctgaaaactc tctgctcagt catggtaggg 840
ccatcagtcc acatgatcag gcctctcctg gccaaacatg gcatctttct tttgggaatt 900
tgaatcttaa gctgaatagc tgaagttcaa aaaaagctgt tgaatctgac ttacgcctac 960
agtggctttg caaagtgact gtccattcct atttcttaag tccctgaatt tataatttat 1020
cctggttaca gccctttctg agatgtgtgg ttttttttcc aactgtctct tatagtctgt 1080
gaattttcat atttcttttc atacattttc atgttttgtt tgtttgtttg tgtgtttttt 1140
ggctttaggt aggcagaatc agtttctgtt gtttataccc aaggaatcct gattgataca 1200
tccttcccct ttaaaaataa agtatctaag gctcaaagag agtaggctac ctgcctgagg 1260
tctgggagta agttagtacc agagctcgta ctaaccccag gttagccaac tgctttacac 1320
aacatttgct ctctccttca gagttatagc agtcttggaa gaaagaagct actattttgc 1380
caaagacctc aggaggacca agaacaagtt ctgggatatg tgatgattga actcttaaaa 1440
agtttgttgg acttctggcc ataattgtgt atctaagacc agatttcatt cttaatagct 1500
aaacaaacaa acaagagatc cacaggttca gcagctataa taagagtgaa ttactgatac 1560
agttgacaac atgaatatat ctcagaaacc atggcatcaa tgagcaaaaa aaatccagac 1620
acagaagaat acgtaccata tgcctgcatt tatgtgatat tctagcattg tattgtccaa 1680
catagtagcc agtagcctca catggctatt caaatttaag ttgattaaaa ttaagtaaga 1740
ataaaaattt agctcttcag tagcgttagc cacatgtaac tagtggctac cacatcagac 1800
ggtgcaaata tagaatattt cctttataac agaaagttct attggaaaac aatgttctag 1860
aaaatataca cataatctat aaaaacaaaa agcaagtcag tgattgtcta aggccagggg 1920
tgaggggaga tcgattgcaa agtggtatga ggaaagtttt ggggtaatag ggttgttgga 1980
atcttgattg cgatgaaggc tactcggtgt ctaatgtgtc acctcctcag actgaacact 2040
tggaattggc gaatttcatt gtatgtaaat tatacctcat aaagtaactc taagaggtca 2100
agtgttttgt ggaaattatt tttaatcagt tgcaatactt attatgagat gatttttgca 2160
aatacataaa catgttattc atccattagg tgcaatattt ttgctagctc ctgaaaacac 2220
agagatgaat tagaatagca agcctgccct caagctgttc acaatccagt acaggagatg 2280
agtctattca aaaatagcta gactccagga agaaagttat aggtgacctt acacaaaaaa 2340
gtgcagatat aattatgtag gacagtagaa gtggggaagg tttcttttat gtggaaaaaa 2400
gagggagaat ttttggtctt tgaaggatga gcaagatgtg aatatgcgca gatggagttt 2460
taaaacattc ctggtggagg gcagaatatg atccaaggca caagagcaac cagaaaaata 2520
tgcaacctag aggaaagtgc atgaagggga gcagttgtaa aataattttc atgaatgtaa 2580
gtgagaagaa tttgtatcat agacacctga gtttggcaga gtgcatgttc ttggctccta 2640
ggagtcaaga agaacaaagt gtccctttct cctacgttat gctcagtggt ccaagtccaa 2700
aacacctttc cttccttaag tactttcttc tcccctccat acaaatctaa agtcttcaca 2760
aacatcattt aaacaggcag gtcatggtca gaaaggcaat tgcttttcct agacttctat 2820
gtacgttatt atattacaat ttctgcctaa aagactctaa agtcttggaa aagtttccac 2880
cttgcacatc aaagatataa ttcatgcatt tgtatagtaa ccttagtccc ctaagagaat 2940
aaggatgaac tataaatata agaagtaatt atggtaatta taatatgatt gccacttatt 3000
tttcacttga tcgtgtatgg ttgcatgcta ctggtgttct gttgaattct agagagtttg 3060

-continued

```
cctctttttc ctgggtcaac tctcgccatt tatttccata atgcaatagg agccaatctt   3120
tttcataatt acttatttaa aatttgttgc catttaattt ctgttcctct tagcttagta   3180
actttaggat ttttaaataa caactattga aatcatgaca tacgtttaaa tgatattatt   3240
taaatacgtt aggctataaa ccttttaaat tttttaaaaa aatagatgag tgtggtggct   3300
catgcctgta atcccaacac tttgggaagc cgggtcggga ggatagcttg agtccagcag   3360
tttgagacca gtcagggcaa cacagcaaga ccccatatct aaaaaaacaa aacaaaacaa   3420
aattacctgg gtatggttgt gctcacctgt agtccaagct acacaggaag ctgaggcaga   3480
aggatcactt gagcccagga ggttgaggct gcagtgatcc atgaacgcgc tgctacactc   3540
agtctgggtg acagtgcaag aagctgtctc aaaaataata aataaataaa aataactttt   3600
aaaaaacaaa aattaattaa attttaaaaa cacaacacac tagagatgtt tgcaaattga   3660
ttatttggga gtctatatcc ctggaagtta atttaaaata tttagaagag ttcttcctca   3720
tttcctagag acgtcgaatt gtaaatatca gagctagaag gaacactagg gctcgccact   3780
ccaaagtgtg gtccaaggac cagcagcatc aagtaacctg ggaacgtgtt agaaatgcag   3840
agtcttaggc ctcaccccag acctactgaa ccagaatctg cattaacaag atttctaggt   3900
gcctcacggg cacattaaaa cttgagaagc tctgcactag aaatcttcac tccacctttc   3960
attataaatg gaatcacttg ggctgtggtc acaggaaatt gattattttt aatttcagaa   4020
ccttctattt aggtcatcta tatttgctaa tagcagggaa gaaagccaaa ctctttaact   4080
gcaattaaca aatctataat taattagtta agcaatcttc cctttaagtt ttacattttg   4140
tggagcaagc tgtttgattt ggctggggct caggccggcc tgtttgtgaa tttcacaatt   4200
cacagatgtt agccgctctc gggctaagta aaggaagaga atgtcaagtt ttaaatagct   4260
tctcccttcc atcctggctg aagcaacaaa taaaatattt ttatgaaaca cattttgagt   4320
tagatttact tacagggaaa tgtcaaattt ctctgaaagg gctttagatt gtctcacaac   4380
tttgacatct actgatgtca cctatttaca ggtgtgtcct gtgactaggg ggtgaaggga   4440
agatgtgaac tcaccatgtt agtgaccgtt agatacacag agtggttttt tttccccctg   4500
ttggagtcta tcctaactga gcttctgaat catatttcat tcaatttcca aatccacaaa   4560
accaggataa gtttacagcc catattcaga aaggaaataa attattttgt gtgtagactt   4620
tcctgatatt acactgattt gggaatatat gaacaatttt atggtttcct ttcgaagtag   4680
gtcaagtcaa agcaaaacca aaaacagcaa aaactgtaag acataaagaa tagagtggag   4740
ccgactgaga gattaaaata aactagaata tttttattaa caggcaattt gaaataattt   4800
gtgcacttca gaatattcta caataatata ttatttccaa ttttaatatc tttaagaaaa   4860
ttactatatt atatgtaagt acatgtgcat gtgtttgagg taggatattt aactcaataa   4920
aggttatttt cttttattcg ggtcaggcaa agcttctaag gggatgtgaa agggatatct   4980
ctttctctta gctgagagga agagtgagtt ctaagttaaa tataatcaag gaatttccct   5040
gtctttgcta tttgagattg tgaccacaac aggcggttgg ctgaaaggga aactgaaggg   5100
cggggaggga gggaaataga tgaaaaaaca aaacaaaaca aaacttccct aagcagctct   5160
acaaaacatt ttagccccag aaatagtcac agaaatcctc aaatcaaacc agtatccaga   5220
tacaaggaag tgttatgtag ctggagcagg gtggacactc atcagctcag ttcagttaca   5280
aaagtccagg ctgctgaaat taaactctga tgccattcat gccagcatcc aatcacgaca   5340
gagatcagaa gttcagagat gcctccagct ccaaattgcc aacaacaagt gtggctacta   5400
```

-continued

```
tacgtcaagg actctgaagc cgtgagagag ggggaagaac aacagtagag aggatgccca   5460

gctggtaaga atcgagtgtt tatgaagttt tagtcaattg atgaatctca ttggctaaaa   5520

tcaagaaacg ctccgcctct ttgcaaatat gtatgaagga gagaagtgcc taaacttcta   5580

tgtctgatag catttgaccc tattgctttt agcctcccgg ctttatatct atatatacac   5640

aggtatttgt gtatatttta tataattgtt ctccgttcgt tgatatcaaa gacagttgaa   5700

ggaaatgaat tttgaaactt cacggtgtgc caccctacag tactgccctg acccttacat   5760

ccagcggtga gtttgaatgt gacataactt ctctcaaaac ttaattgaag tgccttgtgt   5820

attatgaatg tgtcagctgt gtacaaagaa caattcctcc ttgtttagtc agcacagtga   5880

tattattttg gactttctgt ggacttaaag tggtctgtgg acatattttc tgaatgtctt   5940

ttttggttga tatttggatc                                               5960
```

<210> SEQ ID NO 3
<211> LENGTH: 5676
<212> TYPE: DNA
<213> ORGANISM: Homo sapiens

<400> SEQUENCE: 3

```
acggagaaca attatataaa atatacacaa atacctgtgt atatatagat ataaagccgg     60

gaggctaaaa gcaatagggt caaatgctat cagacataga agtttaggca cttctctcct    120

tcatacatat ttgcaaagag gcggagcgtt tcttgatttt agccaatgag attcatcaat    180

tgactaaaac ttcataaaca ctcgattctt accagctggg catcctctct actgttgttc    240

ttccccctct ctcacggctt cagagtcctt gacgtatagt agccacactt gttgttggca    300

atttggagct ggaggcatct ctgaacttct gatctctgtc gtgattggat gctggcatga    360

atggcatcag agtttaattt cagcagcctg gacttttgta actgaactga gctgatgagt    420

gtccaccctg ctccagctac ataacacttc cttgtatctg gatactggtt tgatttgagg    480

atttctgtga ctatttctgg ggctaaaatg ttttgtagag ctgcttaggg aagttttgtt    540

ttgttttgtt ttttcatcta tttccctccc tccccgccct tcagtttccc tttcagccaa    600

ccgcctgttg tggtcacaat ctcaaatagc aaagacaggg aaattccttg attatattta    660

acttagaact cactcttcct ctcagctaag agaaagagat atccctttca catcccctta    720

gaagctttgc ctgacccgaa taaaagaaaa taacctttat tgagttaaat atcctacctc    780

aaacacatgc acatgtactt acatataata tagtaatttt cttaaagata ttaaaattgg    840

aaataatata ttattgtaga atattctgaa gtgcacaaat tatttcaaat tgcctgttaa    900

taaaaatatt ctagtttatt ttaatctctc agtcggctcc actctattct ttatgtctta    960

cagtttttgc tgtttttggt tttgctttga cttgacctac ttcgaaagga aaccataaaa   1020

ttgttcatat attcccaaat cagtgtaata tcaggaaagt ctacacacaa aataatttat   1080

ttcctttctg aatatgggct gtaaacttat cctggttttg tggatttgga aattgaatga   1140

aatatgattc agaagctcag ttaggataga ctccaacagg gggaaaaaaa accactctgt   1200

gtatctaacg gtcactaaca tggtgagttc acatcttccc ttcaccccct agtcacagga   1260

cacacctgta aataggtgac atcagtagat gtcaaagttg tgagacaatc taaagccctt   1320

tcagagaaat ttgacatttc cctgtaagta aatctaactc aaaatgtgtt tcataaaaat   1380

attttatttg ttgcttcagc caggatggaa gggagaagct atttaaaact tgacattctc   1440

ttcctttact tagcccgaga gcggctaaca tctgtgaatt gtgaaattca caaacaggcc   1500

ggcctgagcc ccagccaaat caaacagctt gctccacaaa atgtaaaact taaagggaag   1560
```

-continued

```
attgcttaac taattaatta tagatttgtt aattgcagtt aaagagtttg gctttcttcc   1620
ctgctattag caaatataga tgacctaaat agaaggttct gaaattaaaa ataatcaatt   1680
tcctgtgacc acagcccaag tgattccatt tataatgaaa ggtggagtga agatttctag   1740
tgcagagctt ctcaagtttt aatgtgcccg tgaggcacct agaaatcttg ttaatgcaga   1800
ttctggttca gtaggtctgg ggtgaggcct aagactctgc atttctaaca cgttcccagg   1860
ttacttgatg ctgctggtcc ttggaccaca ctttggagtg gcgagcccta gtgttccttc   1920
tagctctgat atttacaatt cgacgtctct aggaaatgag gaagaactct tctaaatatt   1980
ttaaattaac ttccagggat atagactccc aaataatcaa tttgcaaaca tctctagtgt   2040
gttgtgtttt taaaatttaa ttaatttttg ttttttaaaa gttattttta tttatttatt   2100
atttttgaga cagcttcttg cactgtcacc cagactgagt gtagcagcgc gttcatggat   2160
cactgcagcc tcaacctcct gggctcaagt gatccttctg cctcagcttc ctgtgtagct   2220
tggactacag gtgagcacaa ccatacccag gtaattttgt tttgttttgt tttttttagat   2280
atggggtctt gctgtgttgc cctgactggt ctcaaactgc tggactcaag ctatcctccc   2340
gacccggctt cccaaagtgt tgggattaca ggcatgagcc accacactca tctatttttt   2400
taaaaaattt aaaaggttta tagcctaacg tatttaaata atatcattta aacgtatgtc   2460
atgatttcaa tagttgttat ttaaaaatcc taaagttact aagctaagag gaacagaaat   2520
taaatggcaa caaattttaa ataagtaatt atgaaaaaga ttggctccta ttgcattatg   2580
gaaataaatg gcgagagttg acccaggaaa aagaggcaaa ctctctagaa ttcaacagaa   2640
caccagtagc atgcaaccat acacgatcaa gtgaaaaata agtggcaatc atattataat   2700
taccataatt acttcttata tttatagttc atccttattc tcttagggga ctaaggttac   2760
tatacaaatg catgaattat atctttgatg tgcaaggtgg aaacttttcc aagactttag   2820
agtcttttag gcagaaattg taatataata acgtacatag aagtctagga aaagcaattg   2880
cctttctgac catgacctgc ctgtttaaat gatgtttgtg aagactttag atttgtatgg   2940
aggggagaag aaagtactta aggaaggaaa ggtgttttgg acttggacca ctgagcataa   3000
cgtaggagaa agggacactt tgttcttctt gactcctagg agccaagaac atgcactctg   3060
ccaaactcag gtgtctatga tacaaattct tctcacttac attcatgaaa attattttac   3120
aactgctccc cttcatgcac tttcctctag gttgcatatt tttctggttg ctcttgtgcc   3180
ttggatcata ttctgccctc caccaggaat gttttaaaac tccatctgcg catattcaca   3240
tcttgctcat ccttcaaaga ccaaaaattc tccctctttt ttccacataa aagaaacctt   3300
ccccacttct actgtcctac ataattatat ctgcactttt ttgtgtaagg tcacctataa   3360
ctttcttcct ggagtctagc tatttttgaa tagactcatc tcctgtactg gattgtgaac   3420
agcttgaggg caggcttgct attctaattc atctctgtgt tttcaggagc tagcaaaaat   3480
attgcaccta atggatgaat aacatgttta tgtatttgca aaaatcatct cataataagt   3540
attgcaactg attaaaaata atttccacaa aacacttgac ctcttagagt tactttatga   3600
ggtataattt acatacaatg aaattcgcca attccaagtg ttcagtctga ggaggtgaca   3660
cattagacac cgagtagcct tcatcgcaat caagattcca acaaccctat taccccaaaa   3720
ctttcctcat accactttgc aatcgatctc ccctcacccc tggccttaga caatcactga   3780
cttgcttttt gtttttatag attatgtgta tattttctag aacattgttt tccaatagaa   3840
ctttctgtta taaaggaaat attctatatt tgcaccgtct gatgtggtag ccactagtta   3900
```

-continued

```
catgtggcta acgctactga agagctaaat ttttattctt acttaatttt aatcaactta   3960
aatttgaata gccatgtgag gctactggct actatgttgg acaatacaat gctagaatat   4020
cacataaatg caggcatatg gtacgtattc ttctgtgtct ggattttttt tgctcattga   4080
tgccatggtt tctgagatat attcatgttg tcaactgtat cagtaattca ctcttattat   4140
agctgctgaa cctgtggatc tcttgtttgt ttgtttagct attaagaatg aaatctggtc   4200
ttagatacac aattatggcc agaagtccaa caaacttttt aagagttcaa tcatcacata   4260
tcccagaact tgttcttggt cctcctgagg tctttggcaa aatagtagct tctttcttcc   4320
aagactgcta taactctgaa ggagagagca aatgttgtgt aaagcagttg gctaacctgg   4380
ggttagtacg agctctggta ctaacttact cccagacctc aggcaggtag cctactctct   4440
ttgagcctta gatactttat ttttaaaggg gaaggatgta tcaatcagga ttccttgggt   4500
ataaacaaca gaaactgatt ctgcctacct aaagccaaaa aacacacaaa caaacaaaca   4560
aaacatgaaa atgtatgaaa agaaatatga aaattcacag actataagag acagttggaa   4620
aaaaaaccac acatctcaga aagggctgta accaggataa attataaatt cagggactta   4680
agaaatagga atggacagtc actttgcaaa gccactgtag gcgtaagtca gattcaacag   4740
ctttttttga acttcagcta ttcagcttaa gattcaaatt cccaaaagaa agatgccatg   4800
tttggccagg agaggcctga tcatgtggac tgatggccct accatgactg agcagagagt   4860
tttcagaaga aaataaaggt tctgttaacc aaggaaagag caataggtac agggcagtgg   4920
aaaacaacag atgccaccac aagaggctta aagcagatga tcttgcatgt tccgtagagc   4980
tctggcagcc tgtgactatg agatcagaga aactgaattc ctttgtgtca gggtaactga   5040
acctcaggtc ctagcctttc caggtcatcc tgcatttata gtgaggagag caggaaagaa   5100
ccttcaagga gaggaggtgg tggagtaaat tcaccaacta ttgctcaaat tgaagagact   5160
gagtttggtg atttttaatt gtatgacact tttctgtaca tagctgcagc tcaaccacac   5220
aatctctatt ttagtaaagt ggaagccaaa gttctgtcat ggagaggatc ctgctaactc   5280
ttccaacttt ggacctaata tttgctacag tctgacatcg attaggagta aagctgggcc   5340
tagaacttaa gtaaactgaa tggtattcga atgactttaa ttcaatgaaa aagcaagtgc   5400
attgcaacct tagccatgtg cttcttctga tttgacctcc atctctcttc aggtcactga   5460
aattcatcaa ataaacattt atagttaagt taatgtcaag aagatgcctt aagggagtgt   5520
cccaaggaaa gagggcatgc aagggaacag aggccaattg gggcaggaag aggttggcag   5580
tttctttaac agacaaacct gataccctcc aaagtcacac ccagtgtcca gaagcaatgt   5640
gggtgggctt cttttccaga catccctgaa cagctg                             5676
```

<210> SEQ ID NO 4
<211> LENGTH: 5676
<212> TYPE: RNA
<213> ORGANISM: Homo sapiens

<400> SEQUENCE: 4

```
acggagaaca auuauauaaa auauacacaa auaccugugu auauauagau auaaagccgg     60
gaggcuaaaa gcaauagggu caaaugcuau cagacauaga aguuuaggca cuucucuccu    120
ucauacauau uugcaaagag gcggagcguu ucuugauuuu agccaaugag auucaucaau    180
ugacuaaaac uucauaaaca cucgauucuu accagcuggg cauccucucu acuguuguuc    240
uucccccucu cucacggcuu cagaguccuu gacguauagu agccacacuu guuguuggca    300
auuuggagcu ggaggcaucu cugaacuucu gaucucuguc gugauuggau gcuggcauga    360
```

-continued auggcaucag aguuuaauuu cagcagccug gacuuuugua acugaacuga gcugaugagu 420
guccacccug cuccagcuac auaacacuuc cuuguaucug gauacugguu ugauuugagg 480
auuucuguga cuauuucugg ggcuaaaaug uuuuguagag cugcuuaggg aaguuuuguu 540
uuguuuuguu uuuucaucua uuucccuccc uccccgcccu ucaguuuccc uuucagccaa 600
ccgccuguug uggucacaau cucaaauagc aaagacaggg aaauuccuug auuauauuua 660
acuuagaacu cacucuuccu cucagcuaag agaaagagau aucccuuuca cauccccuua 720
gaagcuuugc cugacccgaa uaaaagaaaa uaaccuuuau ugaguuaaau auccuaccuc 780
aaacacaugc acauguacuu acauauaaua uaguaauuuu cuuaaagaua uuaaaauugg 840
aaauaauaua uuauuguaga auauucugaa gugcacaaau uauuucaaau ugccuguuaa 900
uaaaaauauu cuaguuuauu uuaaucucuc agucggcucc acucuauucu uuaugucuua 960
caguuuuugc uguuuuuggu uuugcuuuga cuugaccuac uucgaaagga aaccauaaaa 1020
uuguucauau auucccaaau caguguaaua ucaggaaagu cuacacacaa aauaauuuau 1080
uuccuuucug aauaugggcu guaaacuuau ccugguuuug uggauuugga aauugaauga 1140
aauaugauuc agaagcucag uuaggauaga cucccaacagg gggaaaaaaa accacucugu 1200
guaucuaacg gucacuaaca uggugaguuc acaucuuccc uucacccccu agucacagga 1260
cacaccugua aauaggugac aucaguagau gucaaaguug ugagacaauc uaaagcccuu 1320
ucagagaaau uugacauuuc ccuguaagua aaucuaacuc aaaauguguu ucauaaaaau 1380
auuuuauuug uugcuucagc caggauggaa gggagaagcu auuuaaaacu ugacauucuc 1440
uuccuuuacu uagcccgaga gcggcuaaca ucugugaauu gugaaauuca caaacaggcc 1500
ggccugagcc ccagccaaau caaacagcuu gcuccacaaa auguaaaacu uaaagggaag 1560
auugcuuaac uaauuaauua uagauuuguu aauugcaguu aaagaguuug gcuuucuucc 1620
cugcuauuag caaauauaga ugaccuaaau agaagguucu gaaauuaaaa auaaucaauu 1680
uccugugacc acagcccaag ugauuccauu uauaaugaaa gguggaguga agauuucuag 1740
ugcagagcuu cucaaguuuu aaugugcccg ugaggcaccu agaaaucuug uuaaugcaga 1800
uucugguuca guaggucugg ggugaggccu aagacucugc auuucuaaca cguucccagg 1860
uuacuugaug cugcuggucc uuggaccaca cuuuggagug gcgagcccua guguuccuuc 1920
uagcucugau auuuacaauu cgacgucucu aggaaaugag gaagaacucu ucuaaauauu 1980
uuaaauuaac uuccagggau auagacuccc aaauaaucaa uuugcaaaca ucucuagugu 2040
guuguguuuu uaaaauuuaa uuaauuuuug uuuuuuaaaa guuauuuuua uuuauuuauu 2100
auuuuugaga cagcuucuug cacugucacc cagacugagu guagcagcgc guucauggau 2160
cacugcagcc ucaaccuccu gggcucaagu gauccuucug ccucagcuuc cuguguagcu 2220
uggacuacag gugagcacaa ccauacccag guaauuuugu uuuguuuugu uuuuuuagau 2280
auggggucuu gcuguguugc ccugacuggu cucaaacugc uggacucaag cuauccuccc 2340
gacccggcuu cccaaagugu ugggauuaca ggcaugagcc accacacuca ucuauuuuuu 2400
uaaaaaauuu aaaagguuua uagccuaacg uauuuaaaua auaucauuua aacguauguc 2460
augauuucaa uaguuguuau uuaaaaaucc uaaaguuacu aagcuaagag gaacagaaau 2520
uaaauggcaa caaauuuuaa auaaguaauu augaaaaaga uuggcuccua uugcauuaug 2580
gaaauaaaug gcgagaguug acccaggaaa aagaggcaaa cucucuagaa uucaacagaa 2640
caccaguagc augcaaccau acacgaucaa gugaaaaaua aguggcaauc auauuauaau 2700

-continued

```
uaccauaauu acuucuuaua uuuauaguuc auccuuauuc ucuuagggga cuaagguuac   2760

uauacaaaug caugaauuau aucuuugaug ugcaaggugg aaacuuuucc aagacuuuag   2820

agucuuuuag gcagaaauug uaauauaaua acguacauag aagucuagga aaagcaauug   2880

ccuuucugac caugaccugc cuguuuaaau gauguuugug aagacuuuag auuuguaugg   2940

aggggagaag aaaguacuua aggaaggaaa gguguuuugg acuuggacca cugagcauaa   3000

cguaggagaa agggacacuu uguucuucuu gacuccuagg agccaagaac augcacucug   3060

ccaaacucag gugucuauga uacaaauucu ucucacuuac auucaugaaa auuauuuuac   3120

aacugcuccc cuucaugcac uuuccucuag guugcauauu uuucugguug cucuugugcc   3180

uuggaucaua uucugcccuc caccaggaau guuuuaaaac uccaucugcg cauauucaca   3240

ucuugcucau ccuucaaaga ccaaaaauuc ucccucuuuu uuccacauaa aagaaaccuu   3300

ccccacuucu acuguccuac auaauuauau cugcacuuuu uuguguaagg ucaccuauaa   3360

cuuucuuccu ggagucuagc uauuuuugaa uagacucauc uccuguacug gauugugaac   3420

agcuugaggg caggcuugcu auucuaauuc aucucugugu uuucaggagc uagcaaaaau   3480

auugcaccua auggaugaau aacauguuua uguauuugca aaaaucaucu cauaauaagu   3540

auugcaacug auuaaaaaua auuuccacaa aacacuugac cucuuagagu uacuuuauga   3600

gguauaauuu acauacaaug aaauucgcca auuccaagug uucagucuga ggaggugaca   3660

cauuagacac cgaguagccu ucaucgcaau caagauucca acaacccuau uaccccaaaa   3720

cuuuccucau accacuuugc aaucgaucuc cccucacccc uggccuuaga caaucacuga   3780

cuugcuuuuu guuuuuauag auuaugugua uauuuucuag aacauuguuu uccaauagaa   3840

cuuucuguua uaaaggaaau auucuauauu ugcaccgucu gaugugguag ccacuaguua   3900

cauguggcua acgcuacuga agagcuaaau uuuuauucuu acuuaauuuu aaucaacuua   3960

aauuugaaua gccaugugag gcuacuggcu acuauguugg acaauacaau gcuagaauau   4020

cacauaaaug caggcauaug guacguauuc uucugugucu ggauuuuuuu ugcucauuga   4080

ugccaugguu ucugagauau auucauguug ucaacuguau caguaauuca cucuuauuau   4140

agcugcugaa ccuguggauc ucuuguuugu uuguuuagcu auuaagaaug aaaucugguc   4200

uuagauacac aauuauggcc agaaguccaa caaacuuuuu aagaguucaa ucaucacaua   4260

ucccagaacu uguucuuggu ccuccugagg ucuuuggcaa aauaguagcu ucuuucuucc   4320

aagacugcua uaacucugaa ggagagagca aauguugugu aaagcaguug gcuaaccugg   4380

gguuaguacg agcucuggua cuaacuuacu cccagaccuc aggcagguag ccuacucucu   4440

uugagccuua gauacuuuau uuuuaaaggg gaaggaugua ucaaucagga uuccuugggu   4500

auaaacaaca gaaacugauu cugccuaccu aaagccaaaa aacacacaaa caaacaaaca   4560

aaacaugaaa auguaugaaa agaaauauga aaauucacag acuauaagag acaguuggaa   4620

aaaaaaccac acaucucaga aagggcugua accaggauaa auuauaaauu cagggacuua   4680

agaaauagga auggacaguc acuuugcaaa gccacuguag gcguaaguca gauucaacag   4740

cuuuuuuuga acuucagcua uucagcuuaa gauucaaauu cccaaaagaa agaugccaug   4800

uuuggccagg agaggccuga ucauguggac ugauggcccu accaugacug agcagagagu   4860

uuucagaaga aaauaaaggu ucuguuaacc aaggaaagag caauagguac agggcagugg   4920

aaaacaacag augccaccac aagaggcuua aagcagauga ucuugcaugu uccguagagc   4980

ucuggcagcc ugugacuaug agaucagaga aacugaauuc cuuuguguca ggguaacuga   5040

accucagguc cuagccuuuc cagguca ucc ugcauuuaua gugaggagag caggaaagaa   5100
```

-continued

```
ccuucaagga gaggaggugg uggaguaaau ucaccaacua uugcucaaau ugaagagacu   5160

gaguuuggug auuuuuaauu guaugacacu uuucuguaca uagcugcagc ucaaccacac   5220

aaucucuauu uuaguaaagu ggaagccaaa guucugucau ggagaggauc cugcuaacuc   5280

uuccaacuuu ggaccuaaua uuugcuacag ucugacaucg auuaggagua aagcugggcc   5340

uagaacuuaa guaaacugaa ugguauucga augacuuuaa uucaaugaaa aagcaagugc   5400

auugcaaccu uagccaugug cuucuucuga uuugaccucc aucucucuuc aggucacuga   5460

aauucaucaa auaaacauuu auaguuaagu uaaugucaag aagaugccuu aagggagugu   5520

cccaaggaaa gagggcaugc aagggaacag aggccaauug gggcaggaag agguuggcag   5580

uuucuuuaac agacaaaccu gauacccucc aaagucacac ccagugucca gaagcaaugu   5640

gggugggcuu cuuuuccaga caucccugaa cagcug                              5676
```

<210> SEQ ID NO 5
<211> LENGTH: 25
<212> TYPE: DNA
<213> ORGANISM: Artificial Sequence
<220> FEATURE:
<223> OTHER INFORMATION: PCR primer

<400> SEQUENCE: 5

```
cgttgatatc aaagacagtt gaagg                                             25
```

<210> SEQ ID NO 6
<211> LENGTH: 26
<212> TYPE: DNA
<213> ORGANISM: Artificial Sequence
<220> FEATURE:
<223> OTHER INFORMATION: PCR primer

<400> SEQUENCE: 6

```
gtccatgcta atctcaatct tgtttg                                            26
```

<210> SEQ ID NO 7
<211> LENGTH: 23
<212> TYPE: DNA
<213> ORGANISM: Artificial Sequence
<220> FEATURE:
<223> OTHER INFORMATION: PCR primer

<400> SEQUENCE: 7

```
ccatgtccca gagcacacag aca                                               23
```

<210> SEQ ID NO 8
<211> LENGTH: 23
<212> TYPE: DNA
<213> ORGANISM: Artificial Sequence
<220> FEATURE:
<223> OTHER INFORMATION: PCR primer

<400> SEQUENCE: 8

```
ctatgggtac actgatcggt ttg                                               23
```

<210> SEQ ID NO 9
<211> LENGTH: 308
<212> TYPE: DNA
<213> ORGANISM: Homo sapiens
<220> FEATURE:
<223> OTHER INFORMATION: gene encoding 5'UTR of p51AmRNA and 165 bases in ORF of p51AmRNA.

<400> SEQUENCE: 9
cgttgatatc aaagacagtt gaaggaaatg aattttgaaa cttcacggtg tgccacccta 60
cagtactgcc ctgaccctta catccagcgt ttcgtagaaa cccagctcat ttctcttgga 120
aagaaagtta ttaccgatcc accatgtccc agagcacaca gacaaatgaa ttcctcagtc 180
cagaggtttt ccagcatatc tgggattttc tggaacagcc tatatgttca gttcagccca 240
ttgacttgaa ctttgtggat gaaccatcag aagatggtgc gacaaacaag attgagatta 300
gcatggac 308

<210> SEQ ID NO 10
<211> LENGTH: 28
<212> TYPE: DNA
<213> ORGANISM: Artificial Sequence
<220> FEATURE:
<223> OTHER INFORMATION: PCR primer

<400> SEQUENCE: 10 tctgggtgacagtgcaagaagctgtctc 28

<210> SEQ ID NO 11
<211> LENGTH: 30
<212> TYPE: DNA
<213> ORGANISM: Artificial Sequence
<220> FEATURE:
<223> OTHER INFORMATION: PCR primer

<400> SEQUENCE: 11 cttcataaacactcgattcttaccagctgg 30

<210> SEQ ID NO 12
<211> LENGTH: 13940
<212> TYPE: DNA
<213> ORGANISM: Artificial Sequence
<220> FEATURE:
<223> OTHER INFORMATION: Plasmid gene containing p51promoter and
      neomycin resistance gene

<400> SEQUENCE: 12
cccgggaggt accgggcccc ccctcgaggt cgacggtatc gataagcttg atctgttcag 60
ggatgtctgg aaaagaagcc cacccacatt gcttctggac actgggtgtg actttggagg 120
gtatcaggtt tgtctgttaa agaaactgcc aacctcttcc tgccccaatt ggcctctgtt 180
cccttgcatg ccctctttcc ttgggacact cccttaaggc atcttcttga cattaactta 240
actataaatg tttatttgat gaatttcagt gacctgaaga gagatggagg tcaaatcaga 300
agaagcacat ggctaaggtt gcaatgcact tgctttttca ttgaattaaa gtcattcgaa 360
taccattcag tttacttaag ttctaggccc agctttactc ctaatcgatg tcagactgta 420
gcaaatatta ggtccaaagt tggaagagtt agcaggatcc tctccatgac agaactttgg 480
cttccacttt actaaaatag agattgtgtg gttgagctgc agctatgtac agaaaagtgt 540
catacaatta aaaatcacca aactcagtct cttcaatttg agcaatagtt ggtgaattta 600
ctccaccacc tcctctcctt gaaggttctt tcctgctctc ctcactataa atgcaggatg 660
acctggaaag gctaggacct gaggttcagt taccctgaca caaaggaatt cagtttctct 720
gatctcatag tcacaggctg ccagagctct acggaacatg caagatcatc tgctttaagc 780
ctcttgtggt ggcatctgtt gttttccact gccctgtacc tattgctctt tccttggtta 840
acagaacctt tattttcttc tgaaaactct ctgctcagtc atggtagggc catcagtcca 900
catgatcagg cctctcctgg ccaaacatgg catctttctt ttgggaattt gaatcttaag 960

-continued

```
ctgaatagct gaagttcaaa aaaagctgtt gaatctgact tacgcctaca gtggctttgc   1020
aaagtgactg tccattccta tttcttaagt ccctgaattt ataatttatc ctggttacag   1080
ccctttctga gatgtgtggt ttttttcca actgtctctt atagtctgtg aattttcata   1140
tttcttttca tacattttca tgttttgttt gtttgtttgt gtgtttttg gctttaggta   1200
ggcagaatca gtttctgttg tttataccca aggaatcctg attgatacat ccttcccctt   1260
taaaaataaa gtatctaagg ctcaaagaga gtaggctacc tgcctgaggt ctgggagtaa   1320
gttagtacca gagctcgtac taaccccagg ttagccaact gctttacaca acatttgctc   1380
tctccttcag agttatagca gtcttggaag aaagaagcta ctattttgcc aaagacctca   1440
ggaggaccaa gaacaagttc tgggatatgt gatgattgaa ctcttaaaaa gtttgttgga   1500
cttctggcca taattgtgta tctaagacca gatttcattc ttaatagcta aacaaacaaa   1560
caagagatcc acaggttcag cagctataat aagagtgaat tactgataca gttgacaaca   1620
tgaatatatc tcagaaacca tggcatcaat gagcaaaaaa aatccagaca cagaagaata   1680
cgtaccatat gcctgcattt atgtgatatt ctagcattgt attgtccaac atagtagcca   1740
gtagcctcac atggctattc aaatttaagt tgattaaaat taagtaagaa taaaaattta   1800
gctcttcagt agcgttagcc acatgtaact agtggctacc acatcagacg gtgcaaatat   1860
agaatatttc ctttataaca gaaagttcta ttggaaaaca atgttctaga aaatatacac   1920
ataatctata aaaacaaaaa gcaagtcagt gattgtctaa ggccaggggt gaggggagat   1980
cgattgcaaa gtggtatgag gaaagttttg gggtaatagg gttgttggaa tcttgattgc   2040
gatgaaggct actcggtgtc taatgtgtca cctcctcaga ctgaacactt ggaattggcg   2100
aatttcattg tatgtaaatt atacctcata aagtaactct aagaggtcaa gtgttttgtg   2160
gaaattattt ttaatcagtt gcaatactta ttatgagatg atttttgcaa atacataaac   2220
atgttattca tccattaggt gcaatatttt tgctagctcc tgaaaacaca gagatgaatt   2280
agaatagcaa gcctgccctc aagctgttca caatccagta caggagatga gtctattcaa   2340
aaatagctag actccaggaa gaaagttata ggtgacctta cacaaaaaag tgcagatata   2400
attatgtagg acagtagaag tggggaaggt ttcttttatg tggaaaaaag agggagaatt   2460
tttggtcttt gaaggatgag caagatgtga atatgcgcag atggagtttt aaaacattcc   2520
tggtggaggg cagaatatga tccaaggcac aagagcaacc agaaaaatat gcaacctaga   2580
ggaaagtgca tgaaggggag cagttgtaaa ataattttca tgaatgtaag tgagaagaat   2640
ttgtatcata gacacctgag tttggcagag tgcatgttct tggctcctag gagtcaagaa   2700
gaacaaagtg tccctttctc ctacgttatg ctcagtggtc caagtccaaa acacctttcc   2760
ttccttaagt actttcttct cccctccata caaatctaaa gtcttcacaa acatcattta   2820
aacaggcagg tcatggtcag aaaggcaatt gcttttccta gacttctatg tacgttatta   2880
tattacaatt tctgcctaaa agactctaaa gtcttggaaa agtttccacc ttgcacatca   2940
aagatataat tcatgcattt gtatagtaac cttagtcccc taagagaata aggatgaact   3000
ataaatataa gaagtaatta tggtaattat aatatgattg ccacttattt ttcacttgat   3060
cgtgtatggt tgcatgctac tggtgttctg ttgaattcta gagagtttgc ctctttttcc   3120
tgggtcaact ctcgccattt atttccataa tgcaatagga gccaatcttt ttcataatta   3180
cttatttaaa atttgttgcc atttaatttc tgttcctctt agcttagtaa ctttaggatt   3240
tttaaataac aactattgaa atcatgacat acgtttaaat gatattattt aaatacgtta   3300
```

-continued

```
ggctataaac cttttaaatt ttttaaaaaa atagatgagt gtggtggctc atgcctgtaa   3360
tcccaacact ttgggaagcc gggtcgggag gatagcttga gtccagcagt ttgagaccag   3420
tcagggcaac acagcaagac cccatatcta aaaaaacaaa acaaaacaaa attacctggg   3480
tatggttgtg ctcacctgta gtccaagcta cacaggaagc tgaggcagaa ggatcacttg   3540
agcccaggag gttgaggctg cagtgatcca tgaacgcgct gctacactca gtctgggtga   3600
cagtgcaaga agctgtctca aaaataataa ataaataaaa ataactttta aaaaacaaaa   3660
attaattaaa ttttaaaaac acaacacact agagatgttt gcaaattgat tatttgggag   3720
tctatatccc tggaagttaa tttaaaatat ttagaagagt tcttcctcat ttcctagaga   3780
cgtcgaattg taaatatcag agctagaagg aacactaggg ctcgccactc caaagtgtgg   3840
tccaaggacc agcagcatca agtaacctgg gaacgtgtta gaaatgcaga gtcttaggcc   3900
tcaccccaga cctactgaac cagaatctgc attaacaaga tttctaggtg cctcacgggc   3960
acattaaaac ttgagaagct ctgcactaga aatcttcact ccacctttca ttataaatgg   4020
aatcacttgg gctgtggtca caggaaattg attattttta atttcagaac cttctattta   4080
ggtcatctat atttgctaat agcagggaag aaagccaaac tctttaactg caattaacaa   4140
atctataatt aattagttaa gcaatcttcc ctttaagttt tacattttgt ggagcaagct   4200
gtttgatttg gctggggctc aggccggcct gtttgtgaat ttcacaattc acagatgtta   4260
gccgctctcg ggctaagtaa aggaagagaa tgtcaagttt taaatagctt ctcccttcca   4320
tcctggctga agcaacaaat aaaatatttt tatgaaacac attttgagtt agatttactt   4380
acagggaaat gtcaaatttc tctgaaaggg ctttagattg tctcacaact ttgacatcta   4440
ctgatgtcac ctatttacag gtgtgtcctg tgactagggg gtgaagggaa gatgtgaact   4500
caccatgtta gtgaccgtta gatacacaga gtggtttttt ttccccctgt tggagtctat   4560
cctaactgag cttctgaatc atatttcatt caatttccaa atccacaaaa ccaggataag   4620
tttacagccc atattcagaa aggaaataaa ttattttgtg tgtagacttt cctgatatta   4680
cactgatttg ggaatatatg aacaatttta tggtttcctt tcgaagtagg tcaagtcaaa   4740
gcaaaaccaa aaacagcaaa aactgtaaga cataaagaat agagtggagc cgactgagag   4800
attaaaataa actagaatat ttttattaac aggcaatttg aaataatttg tgcacttcag   4860
aatattctac aataatatat tatttccaat tttaatatct ttaagaaaat tactatatta   4920
tatgtaagta catgtgcatg tgtttgaggt aggatattta actcaataaa ggttattttc   4980
ttttattcgg gtcaggcaaa gcttctaagg ggatgtgaaa gggatatctc tttctcttag   5040
ctgagaggaa gagtgagttc taagttaaat ataatcaagg aatttccctg tctttgctat   5100
ttgagattgt gaccacaaca ggcggttggc tgaaagggaa actgaagggc ggggagggag   5160
ggaaatagat gaaaaaacaa aacaaaacaa aacttcccta agcagctcta caaaacattt   5220
tagccccaga aatagtcaca gaaatcctca aatcaaacca gtatccagat acaaggaagt   5280
gttatgtagc tggagcaggg tggacactca tcagctcagt tcagttacaa aagtccaggc   5340
tgctgaaatt aaactctgat gccattcatg ccagcatcca atcacgacag agatcagaag   5400
ttcagagatg cctccagctc caaattgcca acaacaagtg tggctactat acgtcaagga   5460
ctctgaagcc gtgagagagg gggaagaaca acagtagaga ggatgcccag ctggtaagaa   5520
tcgagtgttt atgaagtttt agtcaattga tgaatctcat tggctaaaat caagaaacgc   5580
tccgcctctt tgcaaatatg tatgaaggag agaagtgcct aaacttctat gtctgatagc   5640
atttgaccct attgctttta gcctcccggc tttatatcta tatatacaca ggtatttgtg   5700
```

-continued

```
tatattttat ataattgttc tccgttcgtt gatgggggat ccactagttc tagagcggcc   5760
tcgagatcta agtaagcttg gcattccggt actgttggta aaatggaaga cgccaaaaac   5820
ataaagaaag gcccggcgcc attctatcct ctagaggatg gaaccgctgg agagcaactg   5880
cataaggcta tgaagagata cgccctggtt cctggaacaa ttgcttttac agatgcacat   5940
atcgaggtga acatcacgta cgcggaatac ttcgaaatgt ccgttcggtt ggcagaagct   6000
atgaaacgat atgggctgaa tacaaatcac agaatcgtcg tatgcagtga aaactctctt   6060
caattcttta tgccggtgtt gggcgcgtta tttatcggag ttgcagttgc gcccgcgaac   6120
gacatttata atgaacgtga attgctcaac agtatgaaca tttcgcagcc taccgtagtg   6180
tttgtttcca aaaaggggtt gcaaaaaatt ttgaacgtgc aaaaaaaatt accaataatc   6240
cagaaaatta ttatcatgga ttctaaaacg gattaccagg gatttcagtc gatgtacacg   6300
ttcgtcacat ctcatctacc tcccggtttt aatgaatacg attttgtacc agagtccttt   6360
gatcgtgaca aaacaattgc actgataatg aattcctctg gatctactgg gttacctaag   6420
ggtgtggccc ttccgcatag aactgcctgc gtcagattct cgcatgccag agatcctatt   6480
tttggcaatc aaatcattcc ggatactgcg attttaagtg ttgttccatt ccatcacggt   6540
tttggaatgt ttactacact cggatatttg atatgtggat ttcgagtcgt cttaatgtat   6600
agatttgaag aagagctgtt tttacgatcc cttcaggatt acaaaattca aagtgcgttg   6660
ctagtaccaa ccctattttc attcttcgcc aaaagcactc tgattgacaa atacgattta   6720
tctaatttac acgaaattgc ttctgggggc gcacctcttt cgaaagaagt cggggaagcg   6780
gttgcaaaac gcttccatct tccagggata cgacaaggat atgggctcac tgagactaca   6840
tcagctattc tgattacacc cgagggggat gataaaccgg gcgcggtcgg taaagttgtt   6900
ccattttttg aagcgaaggt tgtggatctg gataccggga aaacgctggg cgttaatcag   6960
agaggcgaat tatgtgtcag aggacctatg attatgtccg gttatgtaaa caatccggaa   7020
gcgaccaacg ccttgattga caaggatgga tggctacatt ctggagacat agcttactgg   7080
gacgaagacg aacacttctt catagttgac cgcttgaagt ctttaattaa atacaaagga   7140
tatcaggtgg cccccgctga attggaatcg atattgttac aacaccccaa catcttcgac   7200
gcgggcgtgg caggtcttcc cgacgatgac gccggtgaac ttcccgccgc cgttgttgtt   7260
ttggagcacg gaaagacgat gacggaaaaa gagatcgtgg attacgtggc cagtcaagta   7320
acaaccgcga aaaagttgcg cggaggagtt gtgtttgtgg acgaagtacc gaaaggtctt   7380
accggaaaac tcgacgcaag aaaaatcaga gagatcctca taaaggccaa gaagggcgga   7440
aagtccaaat tgtaaaatgt aactgtattc agcgatgacg aaattcttag ctattgtaat   7500
actgcgatga gtggcagggc ggggcgtaat ttttttaagg cagttattgg tgcccttaaa   7560
cgcctggtgc tacgcctgaa taagtgataa taagcggatg aatggcagaa attcgccgga   7620
tctttgtgaa ggaaccttac ttctgtggtg tgacataatt ggacaaacta cctacagaga   7680
tttaaagctc taaggtaaat ataaaatttt taagtgtata atgtgttaaa ctactgattc   7740
taattgtttg tgtattttag attccaacct atggaactga tgaatgggag cagtggtgga   7800
atgcctttaa tgaggaaaac ctgttttgct cagaagaaat gccatctagt gatgatgagg   7860
ctactgctga ctctcaacat tctactcctc caaaaaagaa gagaaaggta gaagacccca   7920
aggactttcc ttcagaattg ctaagttttt tgagtcatgc tgtgtttagt aatagaactc   7980
ttgcttgctt tgctatttac accacaaagg aaaaagctgc actgctatac aagaaaatta   8040
```

-continued

```
tggaaaaata ttctgtaacc tttataagta ggcataacag ttataatcat aacatactgt   8100
tttttcttac tccacacagg catagagtgt ctgctattaa taactatgct caaaaattgt   8160
gtacctttag ctttttaatt tgtaaagggg ttaataagga atatttgatg tatagtgcct   8220
tgactagaga tcataatcag ccataccaca tttgtagagg ttttacttgc tttaaaaaac   8280
ctcccacacc tccccctgaa cctgaaacat aaaatgaatg caattgttgt tgttaacttg   8340
tttattgcag cttataatgg ttacaaataa agcaatagca tcacaaattt cacaaataaa   8400
gcattttttt cactgcattc tagttgtggt ttgtccaaac tcatcaatgt atcttatcat   8460
gtctggatcc ggctgtggaa tgtgtgtcag ttagggtgtg gaaagtcccc aggctcccca   8520
gcaggcagaa gtatgcaaag catgcatctc aattagtcag caaccatagt cccgccccta   8580
actccgccca tcccgcccct aactccgccc agttccgccc attctccgcc ccatggctga   8640
ctaatttttt ttatttatgc agaggccgag gccgcctcgg cctctgagct attccagaag   8700
tagtgaggag gcttttttgg aggcctaggc ttttgcaaaa agcttcacgc tgccgcaagc   8760
actcagggcg caagggctgc taaaggaagc ggaacacgta gaaagccagt ccgcagaaac   8820
ggtgctgacc ccggatgaat gtcagctact gggctatctg gacaagggaa aacgcaagcg   8880
caaagagaaa gcaggtagct tgcagtgggc ttacatggcg atagctagac tgggcggttt   8940
tatggacagc aagcgaaccg gaattgccag ctggggcgcc ctctggtaag gttgggaagc   9000
cctgcaaagt aaactggatg gctttcttgc cgccaaggat ctgatggcgc aggggatcaa   9060
gatctgatca agagacagga tgaggatcgt ttcgcatgat tgaacaagat ggattgcacg   9120
caggttctcc ggccgcttgg gtggagaggc tattcggcta tgactgggca caacagacaa   9180
tcggctgctc tgatgccgcc gtgttccggc tgtcagcgca ggggcgcccg gttctttttg   9240
tcaagaccga cctgtccggt gccctgaatg aactgcagga cgaggcagcg cggctatcgt   9300
ggctggccac gacgggcgtt ccttgcgcag ctgtgctcga cgttgtcact gaagcgggaa   9360
gggactggct gctattgggc gaagtgccgg ggcaggatct cctgtcatct caccttgctc   9420
ctgccgagaa agtatccatc atggctgatg caatgcggcg gctgcatacg cttgatccgg   9480
ctacctgccc attcgaccac caagcgaaac atcgcatcga gcgagcacgt actcggatgg   9540
aagccggtct tgtcgatcag gatgatctgg acgaagagca tcaggggctc gcgccagccg   9600
aactgttcgc caggctcaag gcgcgcatgc ccgacggcga ggatctcgtc gtgacccatg   9660
gcgatgcctg cttgccgaat atcatggtgg aaaatggccg cttttctgga ttcatcgact   9720
gtggccggct gggtgtggcg gaccgctatc aggacatagc gttggctacc cgtgatattg   9780
ctgaagagct tggcggcgaa tgggctgacc gcttcctcgt gctttacggt atcgccgctc   9840
ccgattcgca gcgcatcgcc ttctatcgcc ttcttgacga gttcttctga gcgggactct   9900
ggggttcgaa atgaccgacc aagcgacgcc caacctgcca tcacgagatt tcgattccac   9960
cgccgccttc tatgaaaggt tgggcttcgg aatcgttttc cgggacgccg gctggatgat  10020
cctccagcgc ggggatctca tgctggagtt cttcgcccac cccgggctcg atcccctcgc  10080
gagttggttc agctgctgcc tgaggctgga cgacctcgcg gagttctacc ggcagtgcaa  10140
atccgtcggc atccaggaaa ccagcagcgg ctatccgcgc atccatgccc ccgaactgca  10200
ggagtgggga ggcacgatgg ccgctttggt cccggatctt tgtgaaggaa ccttacttct  10260
gtggtgtgac ataattggac aaactaccta cagagattta aagctctaag gtaaatataa  10320
aatttttaag tgtataatgt gttaaactac tgattctaat tgtttgtgta ttttagattc  10380
caacctatgg aactgatgaa tgggagcagt ggtggaatgc ctttaatgag gaaaacctgt  10440
```

-continued

```
tttgctcaga agaaatgcca tctagtgatg atgaggctac tgctgactct caacattcta  10500
ctcctccaaa aaagaagaga aaggtagaag accccaagga ctttccttca gaattgctaa  10560
gtttttgag tcatgctgtg tttagtaata gaactcttgc ttgctttgct atttacacca  10620
caaaggaaaa agctgcactg ctatacaaga aaattatgga aaaatattct gtaacctttta  10680
taagtaggca taacagttat aatcataaca tactgttttt tcttactcca cacaggcata  10740
gagtgtctgc tattaataac tatgctcaaa aattgtgtac ctttagcttt ttaatttgta  10800
aaggggttaa taaggaatat ttgatgtata gtgccttgac tagagatcat aatcagccat  10860
accacatttg tagaggtttt acttgcttta aaaaacctcc cacacctccc cctgaacctg  10920
aaacataaaa tgaatgcaat tgttgttgtt aacttgttta ttgcagctta taatggttac  10980
aaataaagca atagcatcac aaatttcaca aataaagcat ttttttcact gcattctagt  11040
tgtggtttgt ccaaactcat caatgtatct tatcatgtct ggatccgtcg accgatgccc  11100
ttgagagcct tcaacccagt cagctccttc cggtgggcgc ggggcatgac tatcgtcgcc  11160
gcacttatga ctgtcttctt tatcatgcaa ctcgtaggac aggtgccggc agcgctcttc  11220
cgcttcctcg ctcactgact cgctgcgctc ggtcgttcgg ctgcggcgag cggtatcagc  11280
tcactcaaag gcggtaatac ggttatccac agaatcaggg gataacgcag gaaagaacat  11340
gtgagcaaaa ggccagcaaa aggccaggaa ccgtaaaaag gccgcgttgc tggcgttttt  11400
ccataggctc cgcccccctg acgagcatca caaaaatcga cgctcaagtc agaggtggcg  11460
aaacccgaca ggactataaa gataccaggc gtttccccct ggaagctccc tcgtgcgctc  11520
tcctgttccg accctgccgc ttaccggata cctgtccgcc tttctccctt cgggaagcgt  11580
ggcgctttct caatgctcac gctgtaggta tctcagttcg gtgtaggtcg ttcgctccaa  11640
gctgggctgt gtgcacgaac cccccgttca gcccgaccgc tgcgccttat ccggtaacta  11700
tcgtcttgag tccaacccgg taagacacga cttatcgcca ctggcagcag ccactggtaa  11760
caggattagc agagcgaggt atgtaggcgg tgctacagag ttcttgaagt ggtggcctaa  11820
ctacggctac actagaagga cagtatttgg tatctgcgct ctgctgaagc cagttacctt  11880
cggaaaaaga gttggtagct cttgatccgg caaacaaacc accgctggta gcggtggttt  11940
ttttgtttgc aagcagcaga ttacgcgcag aaaaaaagga tctcaagaag atcctttgat  12000
cttttctacg gggtctgacg ctcagtggaa cgaaaactca cgttaaggga ttttggtcat  12060
gagattatca aaaaggatct tcacctagat ccttttaaat taaaaatgaa gttttaaatc  12120
aatctaaagt atatatgagt aaacttggtc tgacagttac caatgcttaa tcagtgaggc  12180
acctatctca gcgatctgtc tatttcgttc atccatagtt gcctgactcc ccgtcgtgta  12240
gataactacg atacgggagg gcttaccatc tggccccagt gctgcaatga taccgcgaga  12300
cccacgctca ccggctccag atttatcagc aataaaccag ccagccggaa gggccgagcg  12360
cagaagtggt cctgcaactt tatccgcctc catccagtct attaattgtt gccgggaagc  12420
tagagtaagt agttcgccag ttaatagttt gcgcaacgtt gttgccattg ctacaggcat  12480
cgtggtgtca cgctcgtcgt ttggtatggc ttcattcagc tccggttccc aacgatcaag  12540
gcgagttaca tgatccccca tgttgtgcaa aaaagcggtt agctccttcg gtcctccgat  12600
cgttgtcaga agtaagttgg ccgcagtgtt atcactcatg gttatggcag cactgcataa  12660
ttctcttact gtcatgccat ccgtaagatg cttttctgtg actggtgagt actcaaccaa  12720
gtcattctga gaatagtgta tgcggcgacc gagttgctct tgcccggcgt caatacggga  12780
```

-continued

```
taataccgcg ccacatagca gaactttaaa agtgctcatc attggaaaac gttcttcggg  12840

gcgaaaactc tcaaggatct taccgctgtt gagatccagt tcgatgtaac ccactcgtgc  12900

acccaactga tcttcagcat cttttacttt caccagcgtt tctgggtgag caaaaacagg  12960

aaggcaaaat gccgcaaaaa agggaataag ggcgacacgg aaatgttgaa tactcatact  13020

cttccttttt caatattatt gaagcattta tcagggttat tgtctcatga gcggatacat  13080

atttgaatgt atttagaaaa ataaacaaat aggggttccg cgcacatttc cccgaaaagt  13140

gccacctgac gcgccctgta gcggcgcatt aagcgcggcg ggtgtggtgg ttacgcgcag  13200

cgtgaccgct acacttgcca gcgccctagc gcccgctcct ttcgctttct tcccttcctt  13260

tctcgccacg ttcgccggct ttccccgtca agctctaaat cgggggctcc ctttagggtt  13320

ccgatttagt gctttacggc acctcgaccc caaaaaactt gattagggtg atggttcacg  13380

tagtgggcca tcgccctgat agacggtttt tcgccctttg acgttggagt ccacgttctt  13440

taatagtgga ctcttgttcc aaactggaac aacactcaac cctatctcgg tctattcttt  13500

tgatttataa gggattttgc cgatttcggc ctattggtta aaaaatgagc tgatttaaca  13560

aaaatttaac gcgaatttta acaaaatatt aacgtttaca atttcccatt cgccattcag  13620

gctgcgcaac tgttgggaag ggcgatcggt gcgggcctct tcgctattac gccagcccaa  13680

gctaccatga taagtaagta atattaaggt acgtggaggt tttacttgct ttaaaaaacc  13740

tcccacacct ccccctgaac ctgaaacata aaatgaatgc aattgttgtt gttaacttgt  13800

ttattgcagc ttataatggt tacaaataaa gcaatagcat cacaaatttc acaaataaag  13860

catttttttc actgcattct agttgtggtt tgtccaaact catcaatgta tcttatggta  13920

ctgtaactga gctaacataa                                              13940
```

FIBRIN CITRULLINE DERIVATIVES AND THEIR USE FOR DIAGNOSING OR TREATING RHEUMATOID ARTHRITIS

CROSS-REFERENCE TO RELATED APPLICATIONS

The present application is a 371 application of PCT/FR 00/01857 filed Jun. 30, 2000.

The present invention relates to citrullinated derivatives of fibrin and to their uses in diagnosing and treating rheumatoid arthritis.

Rheumatoid arthritis (hereinafter abbreviated to "RA") is the most common of the forms of chronic inflammatory rheumatism. It is an autoimmune disease; the serum of affected patients contains autoantibodies, some of which are specific and may constitute a marker for this disease, allowing it to be diagnosed even at early stages.

Prior studies by the team of the inventors have shown that these antibodies recognize different molecular forms of the (pro)filaggrin family (for review, cf. for example SERRE and VINCENT, In: Autoantibodies, PETER and SHOENFIELD Eds, Elsevier Science Publishers, 271–276, 1996). These antibodies have, for this reason, been named: "antifilaggrin autoantibodies (AFAs)". Application EP 0 511 116 describes the purification and characterization of antigens of the filaggrin family, recognized by these antibodies, and their use for diagnosing rheumatoid arthritis.

The inventors have shown that the epitopes recognized by the AFAs are carried by regions of the filaggrin molecule, in which at least some of the arginines are deiminated and thus transformed into citrulline; citrullinated peptides specifically recognized by AFAs have thus been obtained from the main immunoreactive regions of filaggrin. These peptides, and their use for diagnosing RA, are the subject of Application PCT/FR97/01541 and of Application PCT/FR98/02899 in the name of BIOMERIEUX. The inventors' observations concerning the role of citrulline residues in the reactivity of filaggrin with RA-specific autoantibodies have subsequently been confirmed by other researchers [SCHELLEKENS et al., Arthritis Rheum., 40, no. 9 supplement, p. S276, summary 1471 (1997); VISSER et al., Arthritis Rheum., 40, no. 9 supplement, p. S289, summary 1551 (1997)].

The inventors have also shown that AFAs represent a considerable proportion of the interstitial immunoglobulins of synovial rheumatoid tissues and that they are synthesized locally by specific plasmocytes present in these tissues, which confirms the hypothesis that they are involved in the autoimmune response associated with RA. The use of filaggrin, or of citrullinated peptides derived therefrom, to neutralize this autoimmune response is the subject of Application PCT/FR98/02900 in the name of UNIVERSITÉ PAUL SABATIER [Paul Sabatier University](TOULOUSE III).

However, the involvement of filaggrin as an immunogen or as a target antigen in the autoimmune response associated with RA has never been noted. The true antigen involved in this response remains to be identified.

The inventors have now succeeded in characterizing this antigen and have thus shown that it is composed of citrullinated derivatives of the α- and/or β-chains of fibrin.

A subject of the present invention is a citrullinated polypeptide derived from all or part of the sequence of the α-chain or of the β-chain of a vertebrate fibrin, by substitution of at least one arginine residue with a citrulline residue.

Preferably, a polypeptide in accordance with the invention comprises at least 5 consecutive amino acids and advantageously at least 10 consecutive amino acids, including at least one citrulline, of the sequence of the α-chain or of the β-chain of a mammalian fibrin. Advantageously, said vertebrate fibrin is a mammalian fibrin, preferably a human fibrin.

Citrullinated polypeptides in accordance with the invention may, for example, be obtained from natural, recombinant or synthetic fibrin or fibrinogen, or from fragments thereof, comprising at least one arginine residue, by the action of peptidyl arginine deiminase (PAD); they may also be obtained by peptide synthesis, directly incorporating one or more citrulline residues into the synthesized peptide.

Citrullinated polypeptides in accordance with the invention may also be pseudopeptides having the same three-dimensional structure, and therefore the same immunological reactivity, as the citrullinated polypeptides derived from the α- or β-chains of fibrin, or from fragments thereof, mentioned above. They may, for example, be pseudopeptides of the retro type, in which L-amino acids are linked together according to a reverse sequence of that of the peptide to be reproduced, or pseudopeptides of the retro-inverso type, consisting of D-series amino acids (instead of the L-series amino acids of natural peptides) linked together according to a reverse sequence of that of the peptide to be reproduced, or alternatively pseudopeptides containing a $CH_2$—NH bond in place of a CO—NH peptide bond. Pseudopeptides of these various types are, for example, described by BENKIRANE et al. [J. Biol. Chem., 270, p. 11921–11926, (1995); J. Biol. Chem., 271, p. 33218–33224, (1996)]; BRIAND et al. [(J. Biol. Chem., 270, p. 20686–20691, (1995); GUICHARD et al. [J. Biol. Chem., 270, p. 26057–26059, (1995)].

A subject of the present invention is also the use of the polypeptides in accordance with the invention, as defined above, for diagnosing RA, in vitro.

The present invention in particular encompasses antigenic compositions for diagnosing the presence of RA-specific autoantibodies in a biological sample, which compositions are characterized in that they contain at least one polypeptide in accordance with the invention, optionally labeled with and/or conjugated to a carrier molecule.

A subject of the present invention is also a method for detecting RA-specific autoantibodies of the G class in a biological sample, which method is characterized in that it comprises:

- bringing said biological sample into contact with at least one polypeptide in accordance with the invention, as defined above, under conditions which allow the formation of an antigen/antibody complex with the RA-specific autoantibodies possibly present;
- detecting, by any suitable means, the antigen/antibody complex possibly formed.

This detection method may be carried out using a kit comprising at least one antigen according to the invention, and also buffers and reagents suitable for constituting a reaction medium which allows the formation of an antigen/antibody complex, and/or means for detecting said antigen/antibody complex.

Said kit may also comprise, where appropriate, reference samples, such as one or more negative serum (sera) and one or more positive serum (sera).

A subject of the present invention is also the use of citrullinated polypeptides in accordance with the invention, for producing a medicinal product, and especially a medicinal product intended to neutralize the autoimmune response associated with RA, and in particular to inhibit the attachment of the humoral or cellular effectors of this autoimmune response, to the citrullinated derivatives of α- or β-chains of fibrin which are present in rheumatoid tissues.

This in vivo neutralization of the autoimmune response may contribute to treating RA or other diseases which are thought to involve lesions induced by an autoimmune response directed against epitopes exhibiting cross-reactions with the citrullinated derivatives of α- or β-chains of fibrin.

Advantageously, for in vivo administration, polypeptides modified so as to prolong their lifetime in the organism, in particular by increasing their resistance to proteases, will be chosen; they may in particular be pseudopeptides, such as those mentioned above.

The present invention also encompasses pharmaceutical compositions, in particular for treating rheumatoid arthritis, characterized in that they contain, as active principle, at least one polypeptide in accordance with the invention.

Pharmaceutical compositions in accordance with the invention may be administered by any suitable means known per se. They may, for example, be administered systemically, orally, parenterally, or by subcutaneous, intravenous or intramuscular injection; they may also be administered locally, for example by intra-articular injections or by microinjections, under arthroscopy, into the inflammatory synovial tissue.

The present invention will be more clearly understood using the additional description which follows, which refers to the identification of deiminated forms of the α-chain or β-chain of human fibrin in rheumatoid tissues, and to the use of deiminated fibrinogen for detecting the presence of AFAs in serum samples.

EXAMPLE 1

Purification and Characterization of Antigenic Proteins Recognized by AFAs in Rheumatoid Synovial Tissues 1) Analysis of Rheumatoid Synovial Tissues Materials and Methods:

The synovial tissue samples used for the protein extractions were taken from patients suffering from rheumatoid arthritis, during a synovectomy or an arthroplasty of the wrist or knee, and all correspond to tissue fragments which are the seat of conventional histological rheumatoid synovitis lesions. They are conserved by freezing in isopentane cooled with liquid nitrogen.

Synovial tissue fragments originating from four patients were extracted sequentially, in a low ionic strength buffer, a urea buffer and in a urea/DTT buffer, successively.

Preparation of Synovial Extracts

The extraction was carried out using an Ultra-Turrax homogenizer (T25 basic, IKA Labortechnik, Staufen, Germany) with a volume of 6 ml of buffer per gram of tissue.

The following buffers were used at a temperature of 0° C.: 40 mM Tris-HCl, pH 7.4, containing 150 mM of NaCl [low ionic strength buffer]; 40 mM Tris-HCl, pH 7.4, containing 8M urea deionized on an ion exchange resin (AG 501-X8, Biorad, Hercules, Calif.) [urea buffer]; 40 mM Tris-HCl, pH 7.4, containing 8M deionized urea and 50 mM dithiothreitol (DTT), (Sigma) [urea/DTT buffer]. All the buffers were supplemented with 20 mM EDTA, 0.02% sodium azide, 2 μg/ml aprotinin, 10 mM N-ethylmaleimide and 1 mM phenylmethylsulfonyl fluoride (Sigma, Saint Louis, Mich.). After each extraction, the homogenates were centrifuged for 20 minutes at 15,000 g, at the temperature of 4° C. The urea buffer and urea/DTT buffer extracts were dialyzed against water before being analyzed by electrophoresis and by immunotransfer.

Electrophoresis and Immunodetection

The synovial proteins of the various extracts were separated by electrophoresis on a 10% polyacrylamide gel in denaturing SDS buffer (SDS-PAGE), and were then electrotransferred onto reinforced nitrocellulose membranes (Hybond-™C extra, Amersham, Little Chalfont, UK).

The membranes were immunodetected with the following antibody preparations; AFA-positive or AFA-negative rheumatoid human sera; non-rheumatoid control human sera derived from patients suffering from other forms of inflammatory rheumatism or from healthy individuals (1/100); purified fractions of AFAs (10 μg/ml); mouse monoclonal antibody directed against human fibrin and fibrinogen (5 μg/ml); two sheep antisera directed, respectively, against recombinant α- and γ-chains of human fibrinogen (1/1000) (Cambio, Cambridge, UK); a rabbit antiserum directed against the recombinant β-chain of human fibrinogen (1/200000) (Cambio).

The human sera used are derived from 95 patients suffering from rheumatoid arthritis (RA), perfectly characterized from a clinical and biological point of view according to the criteria of the American College of Rheumatology, from 24 patients suffering from non-rheumatoid inflammatory rheumatism or from non-inflammatory pathological conditions (control sera) and from 10 healthy individuals. The semi-quantitative titration of the antifilaggrin antibodies (AFAs) in the sera was carried out by indirect imunofluorescence on cryosections of rat esophageal epithelium and by immunotransfer on epidermal extracts enriched in filaggrin acid variant, according to previously published protocols [VINCENT et al., Ann. Rheum. Dis., 48, 712–722 (1989); VINCENT et al., J. Rheumatol., 25, 838–846 (1998)]. The “AFA-positive” sera are those which exhibit AFAs at significant titers after detection using both methods, and the “AFA-negative” sera are those which do not exhibit detectable AFAs by either of the two methods.

The AFAs were purified by affinity chromatography on the epidermal filaggrin acid variant, according to the protocol described by GIRBAL-NEUHAUSER et al. (J. Immunol., 162, 585–594 (1999), using 45 rheumatoid sera having a high AFA titer. The purified antibody fractions were pooled.

Peroxidase-conjugated secondary molecular probes were used for detecting all the primary antibodies: protein A (Sigma), sheep antibodies directed against mouse IgGs (Biosys, Compiègne, France), goat Fab fragments directed against rabbit IgGs (Biosys) and rabbit F(ab')2 fragments directed against sheet IgGs (Southern Biotech. Inc), for detecting, respectively, human, murine, rabbit and sheep IgGs. The peroxidase activity was visualized using the ECL™ detection system (Amersham International, Aylesbury, UK), according to the protocol provided by the manufacturer.

Results

Specific reactivity with the purified AFAs and the AFA-positive rheumatoid sera was observed only in the extract produced in urea/DTT buffer.

The results are illustrated by FIG. 1:

Legend to FIG. 1:

AFAP=purified AFAs;

RA sera=rheumatoid sera:

AFA+=AFA-positive;

AFA−=AFA-negative;

control sera=sera derived from patients suffering from forms of inflammatory rheumatism other than RA, or from healthy donors.

These results show that the specific reactivity with the purified AFAs and the AFA-positive rheumatoid sera relates to two protein bands of apparent molecular weight of approximately 64 kD to approximately 78 kD (w64–78) and of approximately 55 kD to approximately 61 kD (w55–61), respectively. These protein bands were not detected by the AFA-negative sera, regardless of whether they originate from patients suffering from RA or from other forms of inflammatory rheumatism, or are derived from healthy donors.

The presence of these proteins specifically recognized by the purified AFAs and the AFA-positive rheumatoid sera was observed in the urea/DTT extracts of synovial tissues derived from the 4 rheumatoid patients studied.

In total, 48 AFA-positive rheumatoid sera were tested by immunotransfer on at least one synovial urea/DTT extract. Among the sera, 40 recognized w64–78, 39 recognized w55–61, 37 recognized both w64–78 and w55–61, 3 recognized only w64–78 and 2 recognised only w55–61.

Thirteen AFA-negative rheumatoid sera were tested by immunotransfer on at least one urea/DTT extract of synovial tissue; none of these sera recognized either w64–78 or w55–61.

Ten sera derived from healthy donors and 5 sera derived from patients suffering from other forms of inflammatory rheumatism were also tested by immunotransfer on at least one synovial urea/DTT extract; none of these sera recognized either w64–78 or w55–61.

2) Characterization of the w64–78 and w55–61 Antigenic Proteins

The proteins of the urea/DTT buffer extract of the synovial tissue of one of the patients suffering from RA were precipitated with 4 volumes of glacial acetone and then redissolved in the urea/DTT buffer at a concentration 15 times higher than their initial concentration.

The proteins of the concentrated extract were separated by two-dimensional electrophoresis, by isoelectrofocussing followed by SDS-PAGE.

A two-dimensional electrophoretic separation was carried out in the PhastSystem™ (Pharmacia). The first electrophoretic separation was performed on PhastGel™ isoelectrofocussing (IEF) gels which, beforehand, had been washed, dried and rehydrated in a deionized buffer containing 8 M urea, 0.5% Nonidet P-40 and ampholytes creating a pH gradient of 3 to 10 (Pharmacia). The second dimension was performed by SDS-PAGE on 7.5% polyacrylamide gels.

The proteins were then electrotransferred onto polyvinyl difluoride (PVDF) membranes (ProBlott™ membranes, Applied Biosystems, Foster City, Calif.), in 50 mM Tris and 50 mM of boric acid. The membranes were finally stained with an aqueous solution of amido black at 0.1%, of acetic acid at 1% and of methanol at 45%, or immunodetected with rheumatoid sera according to the protocol described in 1) above.

Figure 2:
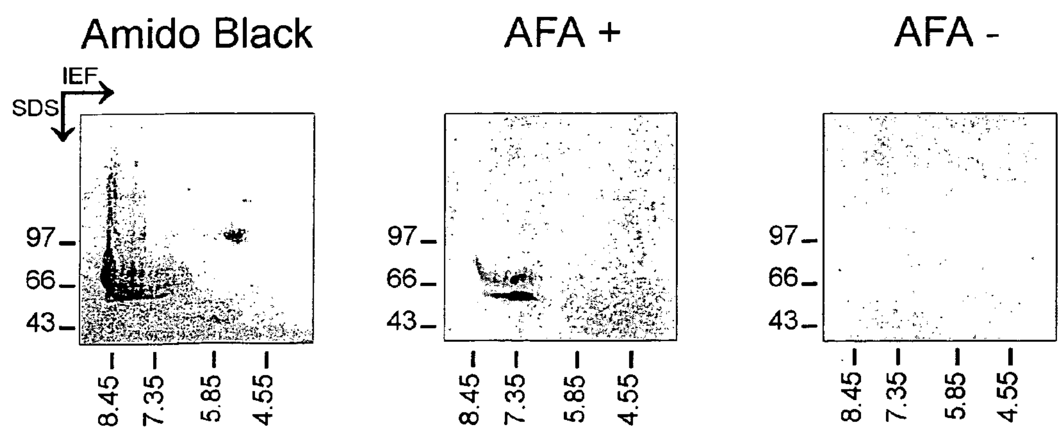

FIG. 2 illustrates the profiles obtained after electrotransfer onto a PVDF membrane and:

a) staining with amido black; or b) immunodetection with an AFA-positive rheumatoid serum; or c) immunodetection with an AFA-negative rheumatoid serum.

Legend to FIG. 2:

Amido Black=staining with amido black;

AFA+=immunodetection with an AFA-positive rheumatoid serum;

AFA−=immunodetection with an AFA-negative rheumatoid serum.

After staining with amido black, the presence of two major proteins, with an apparent molecular weight of 64–78 kD and 55–61 kD and pI of approximately 5.85 to approximately 8.45, is observed.

These proteins are immunodetected with the AFA-positive rheumatoid sera but not with the AFA-negative rheumatoid sera.

Using identical transfers onto a PVDF membrane after two-dimensional electrophoresis, membrane fragments corresponding to the center of each immunoreactive zone were excised and then subjected to amino-terminal sequencing in an Applied Biosystems sequencer (494A or 473A), according to the method recommended by the manufacturer.

The sequence gly-pro-arg-val-val-glu-arg-his-gln-ser-ala (SEQ ID NO.1) was obtained from the membrane fragment corresponding to the w64–78 antigen. This sequence is strictly identical to the sequence 36–46 of the product of the human fibrinogen α-chain precursor gene. When membrane fragments corresponding to the right or left ends of the w64–78 immunoreactive zone were excised and then each subjected to three cycles of amino-terminal sequencing, gly-pro-arg sequences were found each time, indicating that the entire p64–78 immunoreactive zone has the same amino-terminal end.

The sequence gly-his-arg-pro-leu-asp-lys-lys-arg (SEQ ID NO.2) was obtained from the membrane fragment corresponding to the center of the immunoreactive zone corresponding to the w55–61 antigen. This sequence is strictly identical to the sequence 45–54 of the product of the human fibrinogen β-chain precursor gene. When a membrane fragment corresponding to the left end of the w-55–61 immunoreactive zone was excised and then subjected to two cycles of amino-terminal sequencing, the gly-his sequence was found. When a membrane fragment corresponding to the right end of the w55–61 immunoreactive zone was excised and then subjected to six cycles of amino-terminal sequencing, the gly-his-arg-pro-leu-asp sequence and the gly-pro-arg-val-val-glu sequence were found. This indicates that the entire w55–61 immunoreactive zone has the same amino-terminal end and that it partially co-migrates with the w64–78 antigen.

The amino-terminal ends of the w64–78 and w55–61 antigenic proteins correspond, respectively, to the amino-terminal ends of the α- and β-chains of human fibrinogen after respective cleavage, by thrombin, of fibrinopeptides A and B. The amino-terminal ends of the w64–78 and w55–61 antigenic proteins are therefore identical, respectively, to that of the α-chain and to that of the β-chain of human fibrin.

The apparent molecular weights of the w64–78 and w55–61 antigens are compatible with the respective theoretical molecular weight values for the α-chain and for the β-chain of human fibrin.

The identity of the w64–78 antigen and of the α-chain of fibrin, on the one hand, and that of the w55–61 antigen and of the β-chain of fibrin, on the other hand, were confirmed by analyzing the reactivity of antifibrin(ogen) antibodies with respect to these antigens. By immunotransfer, using an extract of synovial tissue prepared in urea/DTT, the "311" mouse monoclonal antibody, which recognizes the three chains α, β and weakly, γ of human fibrinogen and fibrin, is mainly reactive with respect to the w64–78 and w55–61 antigens. Similarly, two antisera, one from sheep and the other from rabbit, directed, respectively, against recombinant α- and β-chains of fibrinogen, recognized mainly a protein which co-migrates with the w64–78 antigen and a protein which co-migrates with the w55–61 antigen, respectively.

EXAMPLE 2

Reactivity of Rheumatoid Sera and of Purified AFAs with deiminated fibrinogen in vitro The reactivity with respect to deiminated and nondeiminated fibrinogen was studied by immunotransfer. The following were used: the purified AFA fractions, 37 AFA-positive rheumatoid sera of decreasing titer, 10 AFA-negative rheumatoid sera and 19 AFA-negative sera derived from patients suffering from forms of inflammatory or non-inflammatory rheumatism (AFA titers determined by immunotransfer on epidermal extracts enriched in filaggrin acid variant).

Figure 3A:
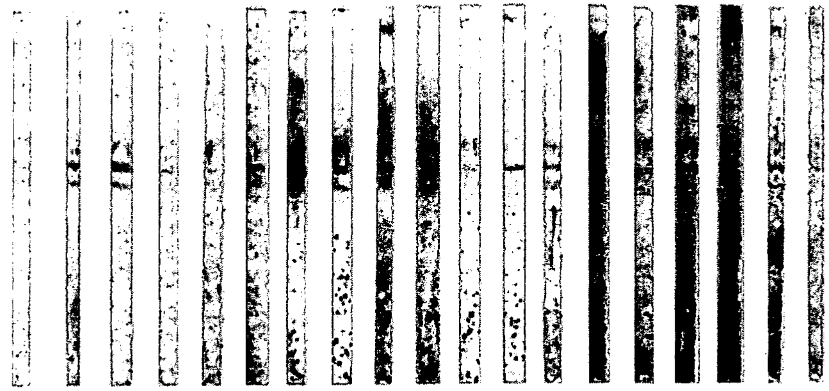
Figure 3A:
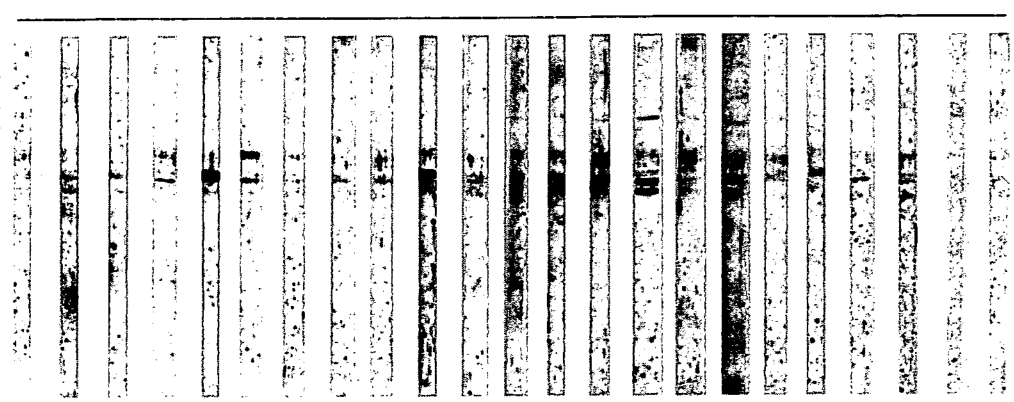
Figure 3A:
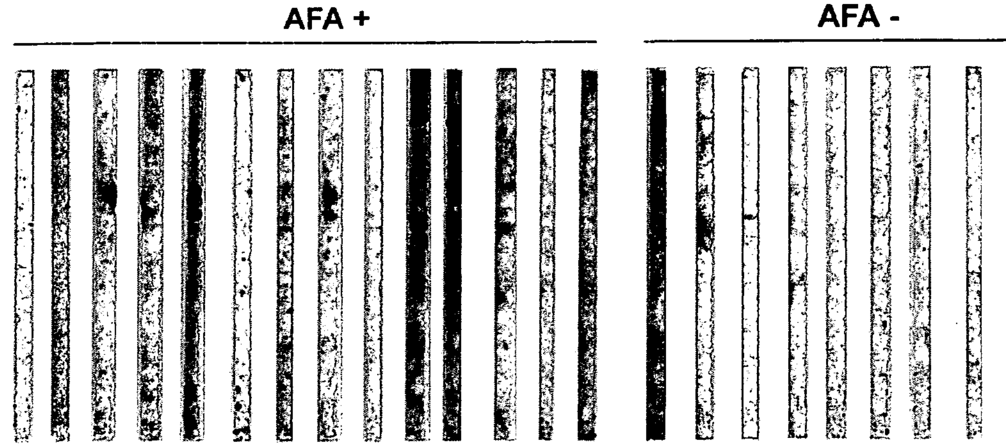
Figure 3A:
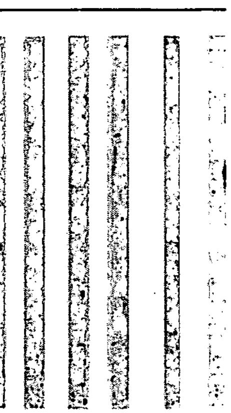
Figure 3B:
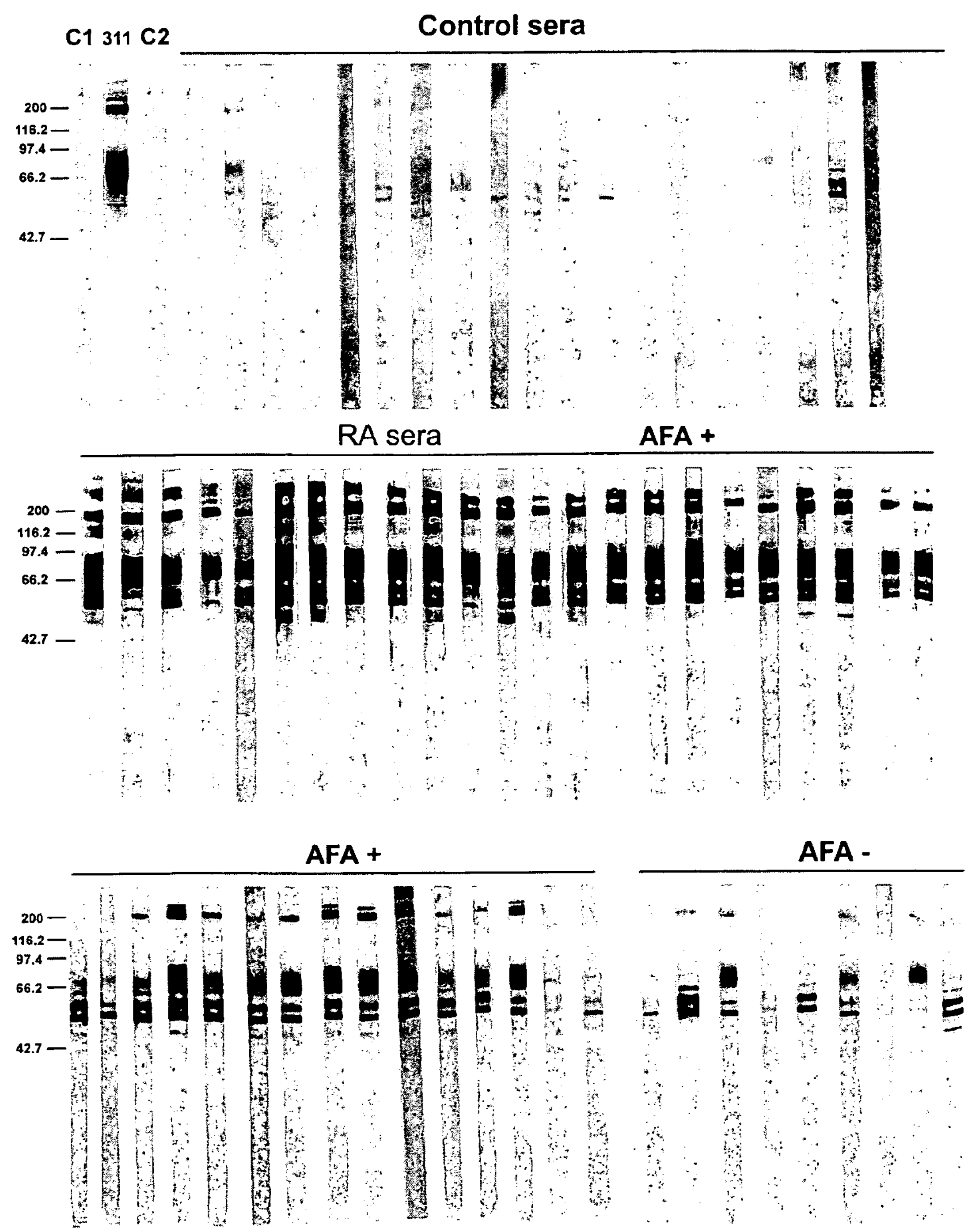

The results are illustrated by FIG. 3A in the case of nondeiminated fibrinogen and by FIG. 3B in the case of deiminated fibrinogen.

Legend to FIG. 3:

FIG. 3A: non deiminated purified human fibrinogen;

311=antifibrinogen monoclonal antibody 311;

control sera=sera derived from patients suffering from forms of inflammatory rheumatism other than RA, or from healthy donors;

RA sera=rheumatoid sera;

AFA+=AFA-positive;

AFA−=AFA-negative;

FIG. 3B: purified human fibrinogen deiminated with a PAD;

311=antifibrinogen monoclonal antibody 311;

C1=sheep antibody directed against mouse IgGs;

C2=sheep antibody directed against protein A;

control sera=sera derived from patients suffering from forms of inflammatory rheumatism other than RA, or from healthy donors;

RA sera=rheumatoid sera;

AFA+=AFA-positive;

AFA−=AFA-negative;

Nondeiminated Fibrinogen

After separation by SDS-PAGE, under the conditions described in example 1 above, the nondeiminated fibrinogen is composed of 3 polypeptides having respective apparent molecular weights 48 kDa, 58 kDa and 69 kDa, corresponding to the expected apparent molecular masses of the α-, β- and γ-polypeptide chains making up the protein (results not given). The "311" antifibrinogen monoclonal antibody strongly recognizes the α- and β-polypeptide chains and very weakly the γ-polypeptide chain (FIG. 3A).

Antisera specific for each of the α-, β- and γ-chains of fibrinogen also showed reactivity with respect to the chain against which they were respectively directed (results not shown).

Deimination of the Fibrinogen

A peptidyl arginine deiminase (PAD) purified from rabbit skeletal muscle (Sigma, St. Louis, Mo.) was used. The human fibrinogen (Calbiochem, San Diego, Calif.) was incubated at the concentration of 0.86 mg/ml, in the presence or absence of PAD (7 U/mg of protein) for 2 h at 50° C., in 0.1 M Tris-HCl buffer, pH 7.4, containing 10 mM of $CaCl_2$ and 5 mM of DTT. These conditions are those which previously made it possible to generate the epitopes on a human recombinant filaggrin, recognized by AFAs [GIRBAL-NEUHAUSER et al., J. Immunol., 162, 585–594 (1999)]. The deimination was then stopped by adding 2% of SDS and heating at 100° C. for 3 min.

After deimination for 2 hours, the electrophoretic mobility by SDS-PAGE of the two α- and β-polypeptides became modified and that of the γ-polypeptide remained unchanged. Specifically, the protein corresponding to the α-chain then appeared in the form of a diffuse band of 82 to 95 kDa and was immunodetected by both the "311" antifibrinogen monoclonal antibody (FIG. 3B) and the antiserum directed against the α-chain of fibrinogen (results not shown).

The protein corresponding to the β-chain appeared in the form of a well-defined doublet with the molecular weight of 458 kD for the lower band and 60 kD for the upper band, which was not recognized by the "311" antifibrinogen monoclonal antibody (FIG. 3B) but was immunodetected by the rabbit antiserum directed against the recombinant β-chain of human fibrinogen (results not shown).

No reactivity for the α-chain or for the β-chain is observed with the C1 and C2 antibodies.

Reactivity of the Sera

The reactivity of the sera with respect to the α- and β-chains of nondeiminated fibrinogen proved to be zero or very weak and concerned only a few sera rarely occurring, belonging to no particular subgroup.

On the other hand, after deimination, the polypeptides corresponding to the deiminated α- and β-chains react strongly with the purified AFAs (results not shown) and with all of the 37 AFA-positive rheumatoid sera (with the exception of that which has the lowest AFA titer). Moreover, 6 AFA-negative rheumatoid sera out of 10 also clearly recognized the deiminated α- or β-polypeptides: 2 immunodetected the α-polypeptide and the β-polypeptide doublet, 3 others only detected the β-polypeptide doublet, and only 1 immunodetected exclusively the α-polypeptide. On the other hand, with the exception of a serum derived from a patient suffering from Sjögren's syndrome, which was reactive on the β-polypeptide doublet, none of the control sera immunodetected the deiminated fibrinogen.

The affinity of the AFA-positive rheumatoid sera with respect to the two deiminated α- and β-polypeptides proved to be slightly variable from one serum to the other. Thus, 6 sera, while strongly detecting the β-polypeptide, only very weakly recognized the α-polypeptide. Similarly, 3 sera, highly reactive with respect to the α-polypeptide, did not detect the deiminated β-polypeptide. Moreover, the intensity of labeling of the two polypeptides appears, overall, to be proportional to the AFA titer of the sera. It should be noted that the sera reactive on the deiminated α and β-polypeptides of fibrinogen were also reactive with respect to high molecular weight (greater than 200 kD) polypeptides generated during the deimination of the fibrinogen. These polypeptides which clearly react with the antifibrinogen antibodies are very probably fibrinogen chain aggregates.

In conclusion, recognition of the α- and β-polypeptides of fibrinogen by rheumatoid sera is not only entirely dependent on their deimination, since the nondeiminated polypeptides are never recognized, but it is also clearly linked to the antifilaggrin reactivity of these sera. It should be noted that these deiminated polypeptides make it possible to detect with great sensitivity the AFAs present in rheumatoid sera.

These results clearly demonstrate that the antigenic targets of the ASAs in rheumatoid synovial joints are deiminated forms of the α-chain and of the β-chain of human fibrin.

What is claimed is:

1. A purified citrullinated polypeptide which reacts with rheumatoid arthritis-specific anti-filaggrin autoantibodies, and is selected from the group consisting of:

a) a citrullinated α-chain of human fibrin;

b) a citrullinated polypeptide resulting from the action of peptidyl arginine deiminase on an α-chain of human fibrinogen; and a fragment of a citrullinated α-chain of human fibrin consisting of at least 5 consecutive amino acids and which also comprises at least one citrulline residue.

2. The purified citrullinated polypeptide according to claim 1, which is a).

3. The purified citrullinated polypeptide according to claim 1, which is b).

4. The purified citrullinated polypeptide according to claim 1, which is c).

5. An antigenic composition for diagnosing the presence of rheumatoid arthritis-specific anti-filaggrin autoantibodies in a biological sample, comprising at least one citrullinated polypeptide as claimed in claim 1, optionally labeled with or conjugated to a carrier molecule.

6. The antigenic composition according to claim 5, wherein said citrullinated polypeptide is labeled.

7. The antigenic composition according to claim 5, wherein said citrullinated polypeptide is conjugated to a carrier molecule.

8. The antigenic composition according to claim 5, wherein said citrullinated polypeptide is a).

9. The antigenic composition according to claim 5, wherein said citrullinated polypeptide is b).

10. The antigenic composition according to claim 5, wherein said citrullinated polypeptide is c).

11. A kit for detecting rheumatoid arthritis-specific anti-filaggrin autoantibodies in a biological sample, comprising at least one polypeptide as claimed in claim 1, and buffers and reagents suitable for constituting a reaction medium which allows the formation of an antigen/antibody complex.

12. The kit according to claim 11, which further comprises reagents for detecting said antigen/antibody complex.

13. A method for detecting rheumatoid arthritis specific anti-filaggrin autoantibodies in a biological sample, which method comprises:

contacting said biological sample with a polypeptide as claimed in claim 1 or combination thereof wherein the formation of an antigen/antibody complex is indicative of the presence of rheumatoid arthritis specific anti-filaggrin autoantibodies.

14. The method according to claim 13, wherein said citrullinated polypeptide is a).

15. The method according to claim 13, wherein said citrullinated polypeptide is b).

16. The method according to claim 13, wherein said citrullinated polypeptide is c).

* * * * *

UNITED STATES PATENT AND TRADEMARK OFFICE

CERTIFICATE OF CORRECTION

PATENT NO. : 7,022,485 B1
APPLICATION NO. : 10/019439
DATED : April 4, 2006
INVENTOR(S) : Guy Serre et al.

It is certified that error appears in the above-identified patent and that said Letters Patent is hereby corrected as shown below:

On the title page, Item (73), the Assignee is incorrect. Item (73) should read:

--(73) Assignee: Biomerieux SA, Marcy l'Etoile (FR)--

Signed and Sealed this

Nineteenth Day of June, 2007

JON W. DUDAS
*Director of the United States Patent and Trademark Office*